United States Patent [19]
Gold et al.

[11] Patent Number: 5,837,456
[45] Date of Patent: Nov. 17, 1998

[54] HIGH AFFINITY OLIGONUCLEOTIDE LIGANDS TO CHORIONIC GONADOTROPIN HORMONE AND RELATED GLYCOPROTEIN HORMONES

[75] Inventors: Larry Gold; Sumedha D. Jayasena, both of Boulder; Dan Nieuwlandt, Broomfield, all of Colo.; Ken Davis, Los Altos, Calif.

[73] Assignee: NeXstar Pharmaceuticals, Inc., Boulder, Colo.

[21] Appl. No.: 488,402

[22] Filed: Jun. 7, 1995

Related U.S. Application Data

[63] Continuation-in-part of Ser. No. 714,131, Jun. 10, 1991, Pat. No. 5,475,096, Ser. No. 931,473, Aug. 17, 1992, Pat. No. 5,270,163, Ser. No. 964,624, Oct. 21, 1992, Pat. No. 5,496,938, Ser. No. 117,991, Sep. 8, 1993, abandoned, and Ser. No. 536,428, Jun. 11, 1990, abandoned.

[51] Int. Cl.⁶ .............................. C12P 19/34; C12Q 1/68; C07H 21/04; C07H 21/02
[52] U.S. Cl. ............................ 435/6; 435/91.2; 536/25.4; 935/77; 935/78
[58] Field of Search ..................... 435/6, 91.2; 536/25.4; 935/77, 78

[56] References Cited

FOREIGN PATENT DOCUMENTS

| 2 183 661 | 6/1987 | United Kingdom . |
|---|---|---|
| WO/89/06694 | 7/1989 | WIPO . |
| 9214843 | 9/1992 | WIPO . |

OTHER PUBLICATIONS

Joyce (1989) Gene 82:83.
Joyce and Inoue (1989) Nucleic Acids Research 17:711.
Ellington and Szostak (1990) Abstract of papers presented at the 1990 meeting on RNA Processin, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Pierce et al. (1981) Annu. Rev. Biochem, 50:465.
Ryan et al. (1988) The FASEB J. 2:2661.
Lustbader et al. (1993) Endocr. Rev. 14:291.
Lapthorn et al. (1994) Nature 369:455.
Dirnhofer et al. (1993)The FASEB J 7:1381.

*Primary Examiner*—Stephanie W. Zitomer
*Attorney, Agent, or Firm*—Swanson & Bratschun LLC

[57] ABSTRACT

Methods are described for the identification and preparation of nucleic acid ligands to CG-related glycoprotein hormones. Included in the invention are specific RNA ligands to hCG and hTSH identified by the SELEX method.

14 Claims, 6 Drawing Sheets

H-25

SEQ ID NO: 43

SEQ ID NO: 117

SEQ ID NO: 80

SEQ ID NO: 41

HIGH AFFINITY OLIGONUCLEOTIDE LIGANDS TO CHORIONIC GONADOTROPIN HORMONE AND RELATED GLYCOPROTEIN HORMONES

RELATED APPLICATIONS

This application is a Continuation-in-Part of U.S. patent application Ser. No. 07/714,131, filed Jun. 10, 1991, entitled Nucleic Acid Ligands now U.S. Pat. No. 5,475,096, U.S. patent application Ser. No. 07/931,473, filed Aug. 17, 1992, entitled Methods for Identifying Nucleic Acid Ligands, now issued as U.S. Pat. No. 5,270,163, U.S. patent application Ser. No. 07/964,624, filed Oct. 21, 1992, entitled Nucleic Acid Ligands to HIV-RT and HIV-1 Rev now U.S. Pat. No. 5,496,938, and U.S. patent application Ser. No. 08/117,991, filed Sep. 8, 1993, entitled High-Affinity Nucleic Acid Ligands Containing Modified Nucleotides, now abandoned. U.S. patent application Ser. No. 07/714,131 is a Continuation-in-Part of U.S. patent application Ser. No. 07/536,428, filed June 11, 1990, entitled Systematic Evolution of Ligands by EXponential Enrichment, now abandoned.

FIELD OF THE INVENTION

Described herein are methods for identifying and preparing high-affinity nucleic acid ligands to chorionic gonadotropin hormone (CG) and related glycoprotein hormones. Chorionic gonadotropin (CG), luteinizing hormone (LH), follicle-stimulating hormone (FSH), and thyroid-stimulating hormone (TSH) constitute a family of glycoprotein hormones. The method utilized herein for identifying such nucleic acid ligands is called SELEX, an acronym for Systematic Evolution of Ligands by EXponential enrichment. Specific examples are provided of oligonucleotides containing nucleotide derivatives chemically modified at the 2'- positions of pyrimidines. Further disclosed are RNA ligands to human chorionic gonadotropin (hCG) containing 2'-$NH_2$-modifications. Also disclosed are specific RNA ligands to human thyroid-stimulating hormone (hTSH) containing 2'-$NH_2$-modifications. Further disclosed are specific RNA ligands to hCG containing 2'-F-modifications. The modified oligonucleotides of the present invention are useful as pharmaceuticals or diagnostic agents.

BACKGROUND OF THE INVENTION

The glycoprotein hormones, LH, FSH, TSH, and CG share similar structural features and have similar mechanisms of action [Pierce and Parsons (1981) Annu. Rev. Biochem. 50:465–495; Ward (1978) in *Structure and Function of the Gonadotropins* (McKerns ed.) Plenum Press, New York, pp 31–46; and Ryan et al. (1988) The FASEB J. 2:2661–2669]. Each hormone is a heterodimer composed of non-covalently associated α and β subunits (Pierce and Parsons (1981) Annu. Rev. Biochem. 50:465–495). In a given species, the alpha subunits are identical, and the beta subunits are different (but homologous) for the different hormones (Rathnam (1981) in *The Radioassay Systems in Clinical Endocrinology* (Abraham ed.) Chap. 2, 21–34; Lustbader et al. (1993) Endocr. Rev. 14:291–311). The β subunit confers specificity to these hormones. In human glycoprotein hormones, there is a high degree of sequence similarity in the first 114 amino acids between hCG and the other hormones (LH 85%, FSH 36%, TSH 46%) (Lapthorn et al. (1994) Nature 369:455–461). The homology between hCG and LH reflects a common biological function, as both proteins bind the same receptor. FSH and TSH bind to structurally similar but distinct receptors (Lapthorn et al. (1994) Nature 369:455–461).

CG, commonly referred to as the "pregnancy hormone," is involved in the maintenance of the early stage of pregnancy in all viviparous mammals (i.e., placental mammals and marsupials) that have been investigated by stimulating the corpus luteum to produce progesterone and relaxin (Lustbader et al. (1993) Endocrine Reviews 14:291–311). Persistence of the corpus luteum is essential since continued secretion of progesterone (and estrogen) is required to sustain the uterine lining and prevent menstruation. Secretion of CG increases rapidly during early pregnancy, reaching a peak at 60 to 80 days after the end of the last menstrual period (Vander et al. (1980) *Human Physiology: The Mechanisms of Body Function*, McGraw Hill Book Company, NY pp. 508–509). By the end of the third month, it has reached a low level which remains relatively constant for the duration of the pregnancy. Concurrent with the decrease in CG secretion, the placenta itself begins to secrete large quantities of progesterone and estrogen. By blocking the biological activity of CG early in pregnancy, the corpus luteum would not be maintained and pregnancy could not be sustained.

In humans, hCG has been selected as a target molecule for a contraceptive vaccine (Dirnhofer et al. (1993) The FASEB J. 7:1381–1385). In order to avoid possible interference by antibodies elicited against hCG with the other glycoprotein hormones, in particular hLH, a synthetic peptide antigen corresponding to the carboxyl-terminal portion of the hCGβ subunit (hCGβCTP) has been developed. hCGβCTP, which comprises the amino acid sequence 109–145, is unique to hCGβ. Although the vaccine should be specific to hCGβ by eliciting hCG-immunoneutralizing antibodies, recent findings suggest that hCGβCTP does not play a role in the biological activity of hCG (Dirnhofer et al. (1993) The FASEB J. 7:1381–1385). Thus, the biological response to hCG was not affected by the antibodies, because the hCG-antibody complex is still able to bind to target cell receptors (Dirnhofer et al. (1993) The FASEB J. 7:1381–1385).

Antibody-based rapid manual tests for the detection of hCG in urine, an indication of pregnancy, are commonly available. Although the presence of elevated levels of hCG is commonly used as a marker for pregnancy, abnormal hCG levels can also be indicative of other clinical conditions. Low serum levels of hCG are often observed in individuals prone to spontaneous abortions. Changes in hCG levels during early pregnancy may indicate ectopic pregnancies, whereas significantly high levels of hCG in the very early stage of pregnancy may help in detecting multiple pregnancies. hCG levels are also known to be reliable markers for monitoring the course of tropoblastic tumors and testicular carcinomas (Saxena (1981) in *The Radioassay Systems in Clinical Endocrinology* (Abraham, G. A., ed.) Chap. 6, 73–99).

hTSH is a glycoprotein with a molecular weight of ~28 kDa and stimulates the synthesis of thyroid hormones. The measurement of serum hTSH levels is important in the diagnosis of both pituitary and thyroid disorders such as hyperthyroidism and hypothyroidism (Saxena (1981) in The Radioassay Systems in Clinical Endocrinology (Abraham, G. A., ed.) Chap. 6, pp 73–99). Ligands that block the biological activity of hTSH may be useful in the treatment of hyperthyroidism by preventing the secretion of T3 and T4.

A method for the in vitro evolution of nucleic acid molecules with high affinity binding to target molecules has been developed. This method, Systematic Evolution of Ligands by EXponential enrichment, termed SELEX, is described in U.S. patent application Ser. No. 07/536,428, entitled Systematic Evolution of Ligands by EXponential Enrichment, now abandoned, United States patent application Ser. No. 07/714,131, filed Jun. 10, 1991, entitled Nucleic Acid Ligands now U.S. Pat. No. 5,476,096, U.S. patent application Ser. No. 07/931,473, filed Aug. 17, 1992, entitled Methods for Identifying Nucleic Acid Ligands, now U.S. Pat. No. 5,270,163 (see also WO91/19813), each of which is herein specifically incorporated by reference. Each of these applications, collectively referred to herein as the SELEX Patent Applications, describe a fundamentally novel method for making a nucleic acid ligand to any desired target molecule.

The SELEX method involves selection from a mixture of candidate oligonucleotides and step-wise iterations of binding, partitioning and amplification, using the same general selection theme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield high affinity nucleic acid ligands to the target molecule.

The basic SELEX method may be modified to achieve specific objectives. For example, U.S. patent application Ser. No. 07/960,093, filed Oct. 14, 1992, entitled Method for Selecting Nucleic Acids on the Basis of Structure, describes the use of SELEX in conjunction with gel electrophoresis to select nucleic acid molecules with specific structural characteristics, such as bent DNA. U.S. patent application Ser. No. 08/123,935, filed Sep. 17, 1993, entitled Photoselection of Nucleic Acid Ligands describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled High-Affinity Nucleic Acid Ligands That Discriminate Between Theophylline and Caffeine, describes a method for identifying highly specific nucleic acid ligands able to discriminate between closely related molecules, termed "counter-SELEX." U.S. patent application Ser. No. 08/143,564, filed Oct. 25, 1993, entitled Systematic Evolution of Ligands by EXponential Enrichment: Solution SELEX, now U.S. Pat. No. 5,567,588 describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or delivery. Examples of such modifications include chemical substitutions at the ribose and/or phosphate and/or base positions. Specific SELEX-identified nucleic acid ligands containing modified nucleotides are described in U.S. patent application Serial No. 08/117,991, filed Sep. 8, 1993, entitled High Affinity Nucleic Acid Ligands Containing Modified Nucleotides, that describes oligonucleotides containing nucleotide derivatives chemically modified at the 5- and 2'-positions of pyrimidines, as well as specific RNA ligands to thrombin containing 2'-amino modifications. U.S. patent application Ser. No. 08/134,028, supra, describes highly specific nucleic acid ligands containing one or more nucleotides modified with 2'-amino (2'- $NH_2$), 2'-fluoro (2'-F), and/or 2'-O-methyl (2'-OMe). Each of these applications is specifically incorporated herein by reference.

BRIEF SUMMARY OF THE INVENTION

The present invention includes methods of identifying and producing nucleic acid ligands to CG and related glycoprotein hormones and the nucleic acid ligands so identified and produced. For the purpose of this application, glycoprotein hormones related to CG include LH, FSH, and TSH. Hereinafter, CG, LH, FSH, and TSH shall be referred to collectively as CG-related glycoprotein hormones. Additionally, human CG shall be referred to as hCG, and hCG-related glycoprotein hormones shall include hCG, hLH, hFSH, and hTSH. The invention includes the specific 2'-$NH_2$ nucleic acid ligands of hCG shown in Tables 2 and 5. The invention further includes the specific 2'-$NH_2$ nucleic acid ligands of hTSH shown in Table 7. The invention further includes the specific 2'-F nucleic acid ligands of hCG shown in FIGS. 3 and 4 and Tables 11 and 13. Specifically, RNA sequences are provided that are capable of binding specifically to hCG or hTSH. Further included in this invention is a method of identifying nucleic acid ligands and nucleic acid ligand sequences to CG-related glycoprotein hormones comprising the steps of (a) preparing a candidate mixture of nucleic acids, (b) contacting the candidate mixture of nucleic acids with the target CG-related glycoprotein hormone, (c) partitioning between members of said candidate mixture on the basis of affinity to the target CG-related glycoprotein hormone, and (d) amplifying the selected molecules to yield a mixture of nucleic acids enriched for nucleic acid sequences with a relatively higher affinity for binding to the target CG-related glycoprotein hormone.

Also included in the invention is the method of identifying nucleic acid ligands and ligand sequences described above wherein the candidate mixture is contacted with one or more non-target molecules so that nucleic acids with affinity to the non-target molecule(s) are removed. Further included in the invention is the method described above wherein the non-target molecule is a CG-related glycoprotein hormone other than the one for which ligands are being selected.

More specifically, the present invention includes the RNA ligands to CG identified according to the above-described method, including those ligands listed in FIGS. 3 and 4 and Tables 2, 5, 11 and 13 (SEQ ID NOS:4–30, 34, 35, 41, 80–160). Also included in the invention are RNA ligands to CG that are substantially homologous to any of the given ligands and that have substantially the same ability to bind CG. Further included in this invention are RNA ligands to CG that have substantially the same structural form as the ligands presented herein and that have substantially the same ability to bind CG.

Additionally, the present invention includes the RNA ligands to TSH identified according to the above-described method, including those ligands listed in Table 7 (SEQ ID NOS:42–63). Also included in the invention are RNA ligands to TSH that are substantially homologous to any of the given ligands and that have substantially the same ability to bind TSH. Further included in this invention are RNA ligands to TSH that have substantially the same structural form as the ligands presented herein and that have substantially the same ability to bind TSH.

The present invention also includes unmodified nucleotide sequences based on the RNA ligands identified herein and mixtures of the same.

DETAILED DESCRIPTION OF THE INVENTION

Figure 1A:
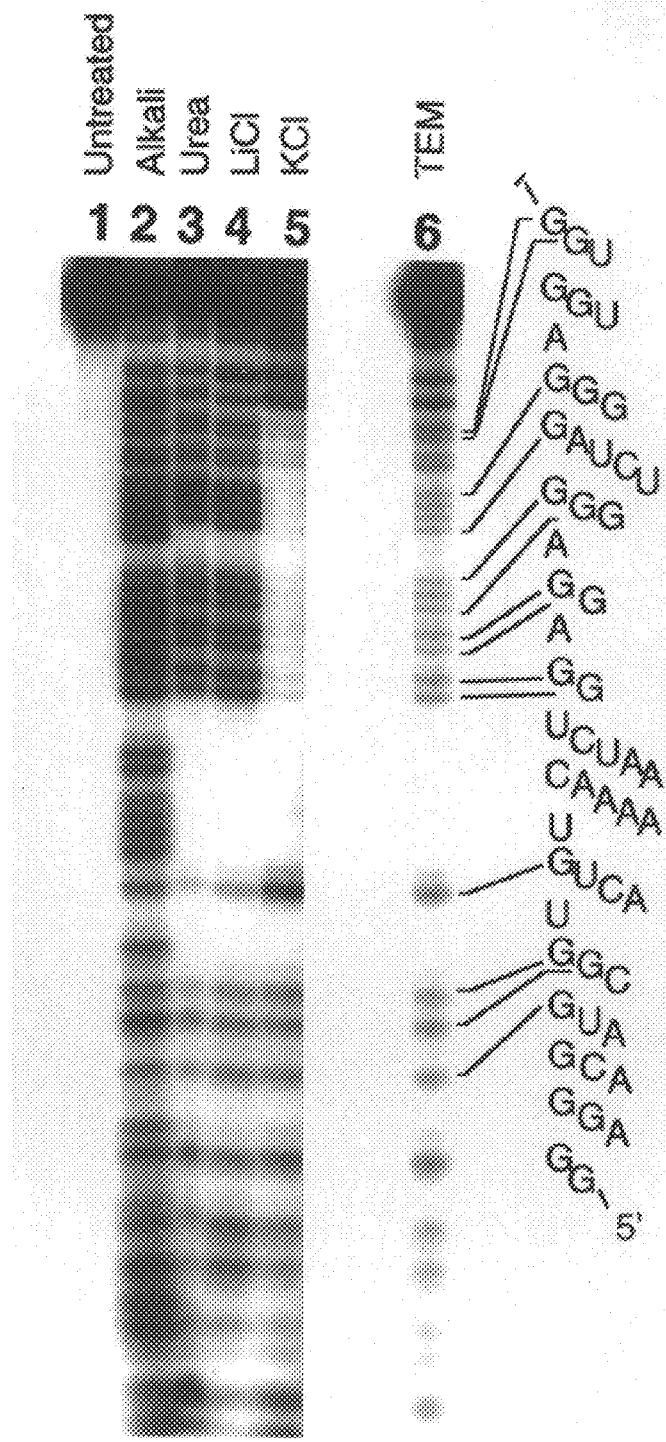
FIGS. 1A–1C show RNase T1 cleavage patterns of 5' end-labeled H-30 (a fragment of SEQ ID NO:7)(I), H-17 (a fragment of SEQ ID NO:19)(II) and H-25 (a fragment of SEQ ID NO:27)(III) RNA analyzed on 8% sequencing gels. Lane 1, untreated end-labeled RNA; lane 2, products of partial alkaline hydrolysis; lane 3, RNase T1 digestion in urea buffer; lane 4, RNase T1 cleavage in LiCl buffer; lane 5, RNase T1 cleavage in KCl buffer. Lane 6 of FIG. 1A shows the RNase T1 cleavage pattern in TEM buffer that was used in SELEX. The right side of each autoradiogram shows the partial sequence of RNA aligned with guanines.

This application describes high-affinity oligonucleotide ligands to CG-related glycoprotein hormones identified through the method known as SELEX.

The SELEX method is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now U.S. Pat. No. 5,475,096, U.S. patent application Ser. No. 07/931,473, filed Aug. 17, 1992, entitled Methods for Identifying Nucleic Acid Ligands, now U.S. Pat. No. 5,270,163, (see also WO91/19813). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligand solutions obtained to a number of target species, including both protein targets where the protein is and is not a nucleic acid binding protein.

The methods described herein and the nucleic acid ligands identified by such methods are useful for both pharmaceutical and diagnostic purposes. Pharmaceutical uses for ligands that block the activity of hCG include birth control in human patients. Pharmaceutical uses for ligands that block the activity of hTSH include treatment of hyperthyroidism by preventing the secretion of T3 and T4. Pharmaceutical uses also include veterinary applications.

Diagnostic utilization may include both in vivo or in vitro diagnostic applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek in a diagnostic ligand. In concurrently filed U.S. patent application Ser. No. 08/487,425 entitled Enzyme-Linked Oligonucleotide Assays ELONAS, the nucleic acid ligands described herein are used in a novel RNA-based sandwich assay for identification of the hCG protein.

SELEX provides high affinity ligands of a target molecule. This represents a singular achievement that is unprecedented in the field of nucleic acids research. The present invention applies the SELEX procedure to CG-related glycoprotein hormones. In the Example section below, the experimental parameters used to isolate and identify the nucleic acid ligands to CG-related glycoprotein hormones are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992 ('624) now U.S. Pat. No. 5,496,938, methods are described for obtaining improved nucleic acid ligands after SELEX has been performed. The '624 application, entitled Methods of Producing Nucleic Acid Ligands, is specifically incorporated herein by reference.

In the present invention, a systematic evolution of ligands by exponential enrichment (SELEX) procedure was used to isolate 2'-NH$_2$-modified RNAs with specific high affinity for hCG from a degenerate library containing 40 random positions (40N) (Examples 1 and 2). RNA truncate studies of a selected ligand were performed to determine the minimal binding domain of a selected 2'-NH$_2$-modified RNA (Example 2). In addition, a SELEX procedure was used to isolate 2'-NH$_2$-modified RNAs with specific high affinity for hTSH from a degenerate library containing 40 random positions (40N) (Example 3). Also in the present invention, a SELEX procedure was used to isolate 2'-F-modified RNAs with specific high affinity to hCG from a degenerate library containing 40 random positions (40N) (Examples 4 and 5). The 5' and 3' boundaries of the minimal 2'-F-modified ligand 9 sequence required for binding hCG was determined (Example 6). A "second generation" SELEX using a conserved 13 nt sequence flanked by 13 nt of contiguous random sequence was performed, and 2'-F-modified RNAs with specific high affinity to hCG were sequenced (Example 7). An hCG ligand dimer was constructed and was shown to have the same affinity for hCG as ligands 9 and 9TR1 (Example 8).

This invention includes the specific RNA ligands to hCG shown in Tables 2 and 5 (SEQ ID NOS:4–30, 34–35), identified by the method described in Example 1. This invention also includes the specific RNA ligands to hTSH shown in Table 7 (SEQ ID NOS:42–63), identified by the method described in Examples 1 and 3. Furthermore, the invention includes the specific RNA ligands to hCG shown in FIGS. 3A, 3B and 4 and Tables 11 and 13 (SEQ ID NOS:41, 80–160) identified by the method described in Examples 4–8. The scope of the ligands covered by this invention extends to all nucleic acid ligands of CG-related glycoprotein hormones, modified and unmodified, identified according to the SELEX procedure. More specifically, this invention includes nucleic acid sequences that are substantially homologous to the RNA ligands shown in FIGS. 3 and 4 and Tables 2, 5, 11 and 13 (SEQ ID NOS:4–30, 34, 35, 41, 80–160). By substantially homologous it is meant a degree of primary sequence homology in excess of 70%, most preferably in excess of 80%. A review of the sequence homologies of the 2'-NH$_2$-modified RNA ligands of hCG shown in Table 2, for example, shows that three groups of nucleic acids have been identified. Within Class I and II, the sequences contain considerable homology; however, in Class III, there is little sequence homology. For these reasons, this invention also includes nucleic acid ligands that have substantially the same ability to bind hCG as the nucleic acid ligands shown in FIGS. 3 and 4 Tables 2, 5, 11 and 13. Substantially the same ability to bind hCG means that the affinity is within one to two orders of magnitude of the affinity of the ligands described herein. It is well within the skill of those of ordinary skill in the art to determine whether a given sequence—substantially homologous to those specifically described herein—has substantially the same ability to bind hCG.

Additionally, this invention also includes nucleic acid ligands that have substantially the same ability to bind hTSH as the nucleic acid ligands shown in Table 7. Substantially the same ability to bind hTSH means that the affinity is within one to two orders of magnitude of the affinity of the ligands described herein. It is well within the skill of those of ordinary skill in the art to determine whether a given sequence—substantially homologous to those specifically described herein—has substantially the same ability to bind hTSH.

This invention also includes the ligands as described above, wherein further chemical modifications are made in order to increase the in vivo stability of the ligand or to enhance or mediate the delivery of the ligand. Examples of such modifications include chemical substitutions at the ribose and/or phosphate and/or base positions of a given nucleic acid sequence. See, e.g., Cook et al. PCT Application WO 92/03568; U.S. Pat. No. 5,118,672 of Schinazi et al.; Hobbs et al. (1973) Biochem. 12:5138; Guschlbauer et al. (1977) Nucleic Acids Res. 4:1933; Shibahara et al. (1987) Nucleic Acids Res. 15:4403; Pieken et al. (1991) Science 253:314, each of which is specifically incorporated herein by reference. Such modifications may be made post-SELEX (modification of previously identified unmodified ligands) or by incorporation into the SELEX process.

The RNA ligands to CG and TSH described herein are useful as pharmaceuticals. This invention, therefore, also includes a method of birth control by administration of a nucleic acid ligand capable of binding to CG. This invention also includes a method of treating hyperthyroidism by administration of a nucleic acid ligand capable of binding TSH.

The following examples are provided to explain and illustrate the present invention and are not to be taken as limiting of the invention.

EXAMPLE 1.

EXPERIMENTAL PROCEDURES FOR 2'-NH$_2$-MODIFIED LIGANDS TO hCG AND hTSH

This Example provides general procedures followed and incorporated into Examples 2–3.

Materials.

2'-NH$_2$-modified pyrimidine NTPs were synthesized as described previously (McGee et al., U.S. patent application Ser. No. 08/264,029 filed Jun. 22, 1994, which is incorporated herein by reference). Oligonucleotides were synthesized by standard cyanoethyl phosphoramidite chemistry. The heterodimer ($M_r$=42,000; 14,000 IU/mg) and the β-subunit ($M_r$=30,000) of hCG were purchased from either Calbiochem or Vitro Diagnostics. hLH ($M_r$=35,500), hTSH ($M_r$=27,700), and hFSH ($M_r$=38,250) were received from Becton Dickinson. The α-subunit of the hormones ($M_r$=14,900) was purchased from UCB-bioproducts. Enzymes were purchased from commercial sources.

SELEX.

A detailed protocol for SELEX has been described in U.S. Pat. No. 5,270,163 (see also Tuerk and Gold (1990) Science 249:505–510). SELEX experiments for hCG and hTSH were initiated with a random sequence pool of RNA in which all pyrimidines were 2'-NH$_2$-modified. Template DNA (5 nmoles) consisting of forty nucleotides of contiguous random sequence flanked by defined sequences for primer annealing (5'-GGGAGGACGATGCGG-(N)$_{40}$-CAGACGACTCGCCCGA-3' (SEQ ID NO:1); Table 1) was amplified by four cycles of polymerase chain reaction (PCR) with 5'-GTAATACGACTCACTATAGGGAGGACG-ATGCGG-3' (SEQ ID NO:2) and 5'-TCGGGCGAGTCGTCTG-3' (SEQ ID NO:3) (Table 1) as primers. For the first round of selection, 800 pmoles of the PCR-derived template DNA (~5×10$^{14}$ molecules) were transcribed in vitro by T7 RNA polymerase (1000 U) in a 3 mL transcription reaction consisting of 2 mM each of ATP, GTP, 2'-NH$_2$CTP and 2'-NH$_2$UTP, 40 mM Tris-HCl (pH 8.0), 12 mM MgCl$_2$, 1 mM Spermidine, 5 mM DTT, 0.002% Triton X-100 and 4% polyethylene glycol (w/v). After incubating overnight at room temperature, the full-length transcription products were purified on 8% denaturing polyacrylamide gels, suspended in TEM buffer (10 mM Tris-HCl, 0.1 mM EDTA, 2.1 mM MgCl$_2$, pH 6.5) (binding buffer), heated to 70° C., chilled on ice, then incubated with the target hormone at 37° C. for 15 minutes The RNA-protein mixture was filtered through a pre-wet nitrocellulose filter then washed with 5 mL of the binding buffer. Bound RNAs were eluted from the filter (Tuerk and Gold (1990) Science 249:505–510) and recovered by ethanol precipitation. The RNA was reverse transcribed by avian myeloblastosis virus reverse transcriptase (Life Sciences) at 48° C. for 45 minutes with 5'-TCGGGCGAGTCGTCTG-3' (SEQ ID NO:3; Table 1) primer. The cDNA was amplified by PCR, and the resulting DNA template was transcribed to obtain RNA for the next round of selection. During the course of SELEX, the concentration of the target hormone was decreased gradually from 3 $\mu$M to 200 nM to progressively increase selective pressure. The selection process was repeated until the affinity of the enriched RNA pool was substantially increased as measured by nitrocellulose filter binding. At that point, cDNA was amplified by PCR with primers that introduced BamHI and Hind III restriction sites at the 5' and 3' ends, respectively. PCR products were digested with BamHI and Hind III and cloned into pUC 18 that was digested with the same enzymes. Individual clones were screened and sequenced by standard techniques (Sambrook et al. in *Molecular Cloning: A laboratory Manual*, 2nd ed., Part 3, pC.1, Cold Spring Harbor Laboratory Press, Cold Spring Harbor, N.Y.).

Determination of equilibrium dissociation constants (K$_d$).

Internally-labeled RNA transcripts were prepared by including [$\alpha$-$^{32}$P]ATP in T7 RNA polymerase transcription reactions. Full-length transcripts were purified on 8% denaturing polyacrylamide gels to ensure size homogeneity. Gel-purified RNA was diluted to a concentration of ~5 nM in TEM buffer, heated to 80° C. then chilled on ice to facilitate secondary structure formation. RNA concentrations were kept lower than 100 pM in binding reactions. Briefly, equal amounts of RNA were incubated with varying amounts of hormone in 50 $\mu$L of TEM buffer for 10 minutes at 37° C. RNA-protein mixtures were passed through pre-wet nitrocellulose filters (0.2$\mu$), and the filters were immediately washed with 5 mL of binding buffer. Radioactivity retained on filters was determined by liquid scintillation counting. The quantities of RNA bound to filters in the absence of protein was determined and used for background correction. The percentage of input RNA retained on each filter was plotted against the corresponding log protein concentration. The nonlinear least square method was used to obtain the dissociation constant (K$_d$) (Jellinek et al. (1993) Proc. Natl. Acad. Sci. U.S.A. 90:11227–11231; Irvine et al. (1991) J. Mol. Biol. 222:739–761).

Minimal sequence determination.

Gel-purified RNA transcripts were labeled at either the 5' ends (with [$\gamma$-$^{32}$P]ATP and T4 polynucleotide kinase) or at the 3' ends (with [5'-$^{32}$P]pCp and RNA ligase) and labeled RNAs were repurified on 8% denaturing at 70° C. for 5 minutes in a buffer consisting of 50 mM sodium carbonate (pH 9.0), 1 mM EDTA and 5 $\mu$g/$\mu$L tRNA. The reaction products were recovered by ethanol precipitation and resuspended in TEM buffer. Partially hydrolyzed RNA was selectively bound to hCG at 25, 50 and 100 nM before being separated on nitrocellulose filters. RNA fragments retained on filters were recovered and resolved on 8% sequencing gels.

RNase T1 cleavage.

Ten pmoles of 5' end-labeled RNA was suspended in 50 $\mu$L of a) RNase T1 buffer [7M urea, 20 mM sodium citrate and 1 mM EDTA (pH 5.0)]; b) 10 mM Tris-HCl, 1 mM MgCl$_2$, 10 mM LiCl (pH 6.5) ; c) 10 mM Tris-HCl, 1 mM MgCl$_2$, 10 mM LiCl (pH 6.5). RNA suspensions were heated to 70° C. and cooled to ambient temperature. RNA was digested with 0.2 U of RNase T1 at 37° C. for 10 minutes and recovered by ethanol precipitation. Cleavage products were resolved on 8% sequencing gels.

Native polyacrylamide gel electrophoresis.

Internally-labeled RNA (~50 pmoles) was suspended either in 10 mM Tris-HCl, 1 mM MgCl$_2$ and 50 mM KCl (pH 6.5) buffer or in 10 mM Tris-HCl, 1 mM MgCl$_2$ and 50 mM LiCl (pH 6.5) buffer, heated to 70° C. and cooled to ambient temperature. The RNA was then loaded onto 8% native polyacrylamide gels prepared in standard TBE buffer containing 50 mM KCl or LiCl. Gels were run at <10 mA for several hours at ambient temperature.

For duplex competition experiments, RNA was mixed with a 200-fold excess of gel-purified, synthetic oligodeoxynucleotides before being subjected to heating and cooling.

EXAMPLE 2.

2'-NH$_2$-MODIFIED RNA LIGANDS FOR hCG

The random RNA pool did not show detectable binding to hCG in PBS buffer at hCG concentrations as high as 5 $\mu$M, under nitrocellulose filter binding conditions. However, reasonable binding (K$_d$~2.5 $\mu$M) of the random pool was observed in low salt TEM buffer (10 mM Tris-HCl, 0.1 mM EDTA, 2.1 mM MgCl$_2$, pH 6.5). The affinity of the enriched pool was improved significantly after nine rounds of SELEX in TEM buffer (K$_d$~50 nM). Table 2 shows the sequences of individual clones derived from the PCR products after the 9th round. Out of 40 sequences analyzed, 25 were unique. Individual sequences were categorized into three classes (Table 2) on the basis of sequence similarities. In the full-length RNA molecules, the variable sequence is flanked by 5'-fixed (5'-GGGAGGACGAUGCGG- (SEQ ID NO:31)) and 3'-fixed (-CAGACGACUCGCCCGA-3' (SEQ ID NO:32)) sequences, which are set forth at the top of the table. The number of clones carrying the same sequence is shown in parentheses. All pyrimidines have 2'-NH$_2$-modified sugars. Two conserved sequence elements that are closely related can be identified in Classes I and II (enclosed by boxes). The conserved sequence of Class II, A/U GGG A/U ACGCG GAGGGG U/A (SEQ ID NO:25) in fact, represents the 3' region of the conserved sequence of Class I, U/AG A/U GGAGGGUACGUGGAGGGG U/A (SEQ ID NO:17). The conserved sequence elements of these two classes appear in different locations within the variable region.

Affinity and Specificity.

Representative ligands from all three classes were characterized in terms of their affinities for hCG (Table 3). $K_d$'s were measured by nitrocellulose filter binding as described in Example 1. $K_d$'s between 4 and 44 nM were observed when the ligands were assayed for binding to hCG in TEM or TESM (TEM+100 mM NaCl) buffer by nitrocellulose filter binding. However, no binding was observed in the absence of $Mg^{++}$ ions. An approximately equal affinity for hLH was observed with all sequences investigated. Based on the high degree of structural similarity between hCG and hLH, this result is not surprising. On the other hand, these ligands do not bind with high affinity to hFSH or hTSH ($K_d$'s are >1 μM; Table 3), suggesting that the β-subunit is involved in RNA binding. By incorporating a counterselection step, SELEX allowed the isolation of hCG-specific RNA ligands (Example 5, infra). Ligand H-42 (SEQ ID NO:5) binds weakly to the conserved α-subunit alone ($K_d \sim 1.4$ μM). The affinity of this ligand to the β-subunit of hCG is about 30-fold lower ($K_d \sim 200$ nM) than to the heterodimer and about seven-fold higher than the affinity for the α-subunit. The lack of high-affinity binding to hTSH and hFSH may therefore suggest that the ligand binding site is not exclusively on the α-subunit.

Truncated ligands.

RNA molecules with the minimum sequence information required for high-affinity binding were sought. In these experiments, two sets of nested fragments were generated by partial alkaline hydrolysis of full-length RNAs radiolabeled at either the 5' or the 3' end. These fragments were challenged with hCG, and bound fragments were recovered by nitrocellulose filter binding and resolved on sequencing gels.

The results of an experiment initiated with the 5' end-labeled H-25 (SEQ ID NO:27) RNA show that the smallest fragment retained by hCG at all concentrations used terminates with $G_{32}$ (indicated by the asterisk in Table 4). The lack of alkaline hydrolysis at pyrimidines makes it difficult to identify the boundary to the single nucleotide level. However, the results suggest that nucleotides beyond $G_{32}$ (toward the 3' end) are not involved in high-affinity binding and can be disposed of. The analogous experiment carried out with 3'-end labeled H-25 gave no apparent boundary, suggesting that the entire 5'-region of the RNA molecule is required for high-affinity binding.

Based on the information boundary analysis, a 34-nucleotide (nt) truncated H-25 RNA (Δ25; SEQ ID NO:34) was constructed and its affinity for hCG was determined. As shown in Table 5, the $K_d$ of Δ25 is ~25 nM, four-fold higher than the 71 nt full-length molecule. A truncated version of a class II RNA, H-17 (Δ17; SEQ ID NO:35), that contains the 5'-fixed region followed by the 17 nt-long conserved region, also binds with a $K_d$ of 25 nM (Table 5).

Secondary Structure.

Conserved sequence elements identified in both Class I and II, as well as, the high affinity-binding truncated version of a Class III ligand, are all rich in guanines. No apparent stable stem-loop structures can be identified within these G-rich RNA molecules. The G-rich nature of these sequences suggested the possibility of forming G-quartet structures. In a G-quartet, four guanines arrayed in a square planer configuration are held together by hydrogen bonding.

Figure 1B:
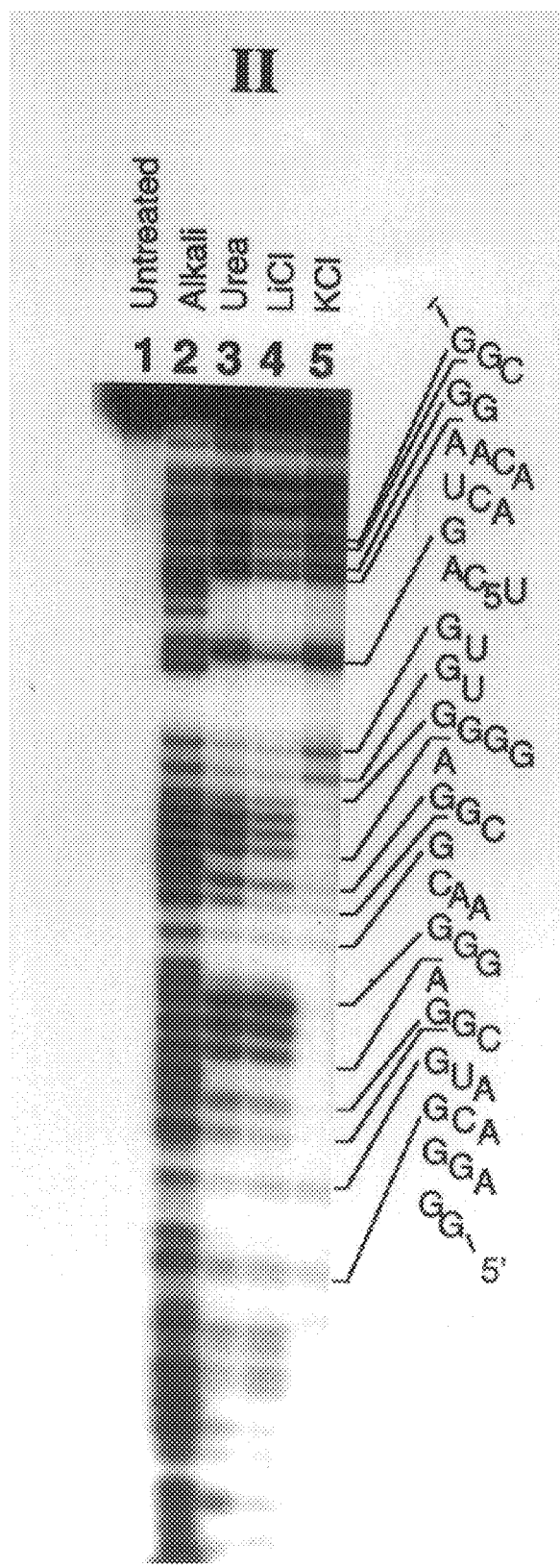
Figure 1C:
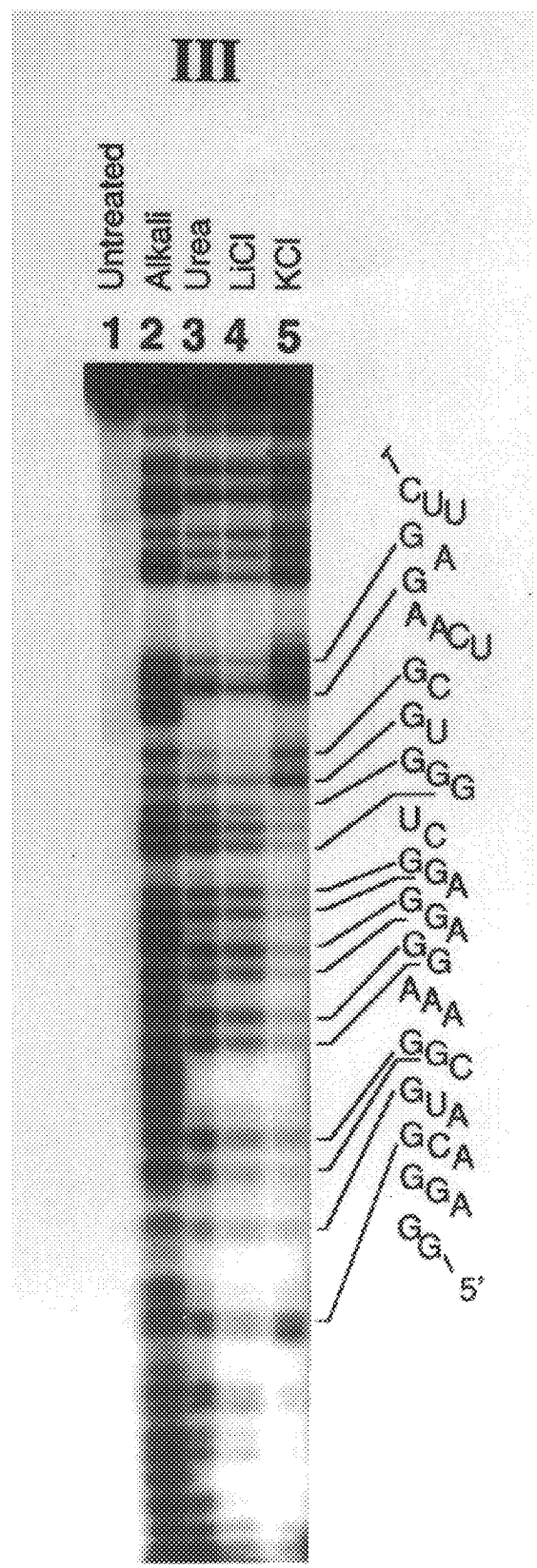

We have previously used RNase T1 as a probe to identify G-quartet structures in RNA (Lyn et al. submitted). Guanines involved in a G-quartet structure show resistance toward RNase $T_1$ cleavage. FIGS. 1A–1C show the RNase T1 cleavage patterns of three representative ligands from the three classes (I, H-30 (SEQ ID NO:7); II, H-17 (SEQ ID NO:19), and III, H-25 (SEQ ID NO:27)). Untreated end-labeled RNA is shown in lane 1; products of partial alkaline hydrolysis are shown in lane 2; RNase $T_1$ digestion in urea [(7M urea, 20 mM sodium-citrate, 1 mM EDTA, pH 5.0)] is shown in lane 3; RNase $T_1$ cleavage in TEM buffer containing 10 mM $Li^+$ ions [(10 mM Tris-HCl, 1 mM $MgCl_2$, 10 mM LiCl, pH 6.5)] is in lane 4; RNase T1 cleavage in TEM buffer containing 10 mM $K^+$ ions [(10 mM Tris-HCl, 1 mM $MgCl_2$, 10 mM KCl, pH 6.5)] is shown in lane 5. Lane 6 of I shows the RNase T1 cleavage pattern in TEM buffer that was used in SELEX. The right side of each autoradiogram shows the partial sequence of RNA aligned with guanines.

In all three cases, certain guanines are protected by RNase T1 in the presence of $K^+$ ions, but not in either urea or $Li^+$ buffers. For example, in the H-30 sequence, guanines close to the middle of the sequence become RNase T1-resistant in the presence of $K^+$ ions, but not in $Li^+$ urea buffer. These guanines are all located in the conserved sequence with the exception of four additional guanines toward the 3' end. However, guanine doublets in the 5'-fixed region are not protected. In ligand 17, on the other hand, contiguous guanines from the 5'-fixed region up to the 3'-boundary of the conserved region remain protected in $K^+$ buffer. The reactivity of single guanines within this region, or of contiguous guanines found beyond this region, are not affected. In the H-25 sequence, contiguous guanines in the variable region as well as in the 5'-fixed region are protected in $K^+$ buffer. Triangles in Table 6 indicate the guanines in each sequence that became protected in the KCl buffer.

The RNase T1 protection data alone is not sufficient to determine whether the putative G-quartet structures in these RNA molecules arise from either inter- or intramolecular interactions. This can be discerned, however, by the gel mobility patterns of these ligands under native conditions. For gel mobility studies, we used the truncated ligands Δ17 (SEQ ID NO:35) and Δ25 (SEQ ID NO:34) (Table 5). Both Δ17 and Δ25 exhibited electrophoretic patterns in LiCl buffer consistent with their size. However, in KCl buffer, the two RNA sequences migrated faster than they did in LiCl buffer. The observed high mobility of $K^+$ ions can be explained by the formation of intramolecular G-quartets with a compact structure. This result is in agreement with previously published data on telomeric sequences that form intramolecular G-quartets (Williamson et al. (1989) Cell 59:871–880). Species migrating slower than expected for their size should be observed if intermolecular G-quartets are formed (Awang et al. (1993) Biochemistry 32:11453–11457).

To further determine whether the increased mobility of RNA in the KCl buffer is in fact due to the formation of G-quartets, we looked at the mobility in the presence of three different short oligodeoxynucleotides complementary to three regions (5', middle and 3'-) of the Δ25 sequence. These oligonucleotides can potentially hybridize to three G-rich sites, thus preventing G-quartet formation. Δ25 RNA migrated slower in the presence of any of the three oligonucleotides as compared to the RNA alone. This result suggests that the complementary DNA competes with G-quartet formation by forming short duplexes. As a control, the gel mobility of ligand Δ17 in the presence of the three oligonucleotide sequences was also investigated. Of the three oligonucleotides, only the 5' sequence can hybridize to the 5'-region of Δ17 RNA. Consistent with hybridization, only the 5'-DNA sequence decreased the gel mobility of Δ17. The above results collectively support the formation of intramolecular G-quartet structures in the 2'-NH$_2$-modified RNA ligands selected for hCG.

Due to the presence of several guanine doublets within the two truncated sequences Δ17 and Δ25, an intramolecular G-quartet structure will contain two G-planes. The presence of more than four guanine doublets potentially allows the formation of more than one intramolecular G-quartet. The RNase T1 protection data identified G-quartet motifs within a long RNA molecule, but was insufficient for mapping the individual guanines that participate in the structure. With existing data, the accurate assignment of loop residues and the guanine doublets that form the guanine planes is difficult.

Effect of pH on hCG binding.

It has previously been shown that the affinity of a 2'-NH$_2$-modified ligand to its target protein can be especially pH sensitive. This phenomenon may arise from a change in the ionization state of either the target protein or the RNA ligand or both. The ionization state of a 2'-NH$_2$-modified RNA is especially sensitive to pH due to the pK$_a$ of the 2'-NH$_2$ group [pK$_a$~6 (Miller et al. (1993) Nucleosides and Nucleotides 12:785–792; Guschlbauer and Jankowski (1980) Nucleic Acids Res. 8:1421–1433)]. The binding affinity and specificity of the H-42 (SEQ ID NO:5) ligand changes with changes in pH; above pH 6.5, the K$_d$ for hCG increases dramatically (>25-fold at pH 7.0), whereas the change in affinity for hLH is minimal (<2-fold) (data not shown).

EXAMPLE 3.

2'-NH$_2$-MODIFIED RNA LIGANDS TO hTSH
SELECTION OF 2'-NH$_2$-MODIFIED RNA LIGANDS TO hTSH

Analogous to hCG binding described in Example 2, the 2'-NH$_2$-modified random sequence RNA pool bound to hTSH with a K$_d$ of >2.5 μM in TEM buffer. After nine rounds of SELEX in TEM, the K$_d$ of the enriched pool was approximately 30 nM, a significant improvement in affinity. The PCR products after the 9th round of selection were cloned and individual clones were sequenced. The aligned sequences are shown in Table 7. In the full-length RNA molecules, the variable sequence is flanked by 5'-fixed (5'-GGGAGGACGAUGCGG-) (SEQ ID NO:31) and 3'-fixed (-CAGACGACUCGCCCGA-3) (SEQ ID NO:32) sequences, which are shown at the top of the table. All pyrimidines have 2'-NH$_2$-modified sugars. A short sequence (boxed) conserved among all ligands was identified.

Affinity and Specificity.

Selected ligands bind hTSH with K$_d$'s in the range of 15–80 nM. Table 8 shows the observed K$_d$ values obtained from binding curves with a representative ligand (T-15 (SEQ ID NO:43)) and hormones hTSH, hLH, hCG, and hFSH, and with the two individual subunits (alpha and beta). As indicated by the K$_d$ values (Table 8), the specificity of ligand T-15 for hTSH is quite high. Ligand T-15 did not bind with high affinity to the individual α and β subunits, suggesting that this ligand binding site may consist of residues from both subunits. Unlike the hCG ligands, the affinity of ligand T-15 for hTSH was not significantly affected by changes in the pH of the medium (pH range of 5.8–7.2; data not shown).

Secondary Structure of hTSH.

Figure 2:
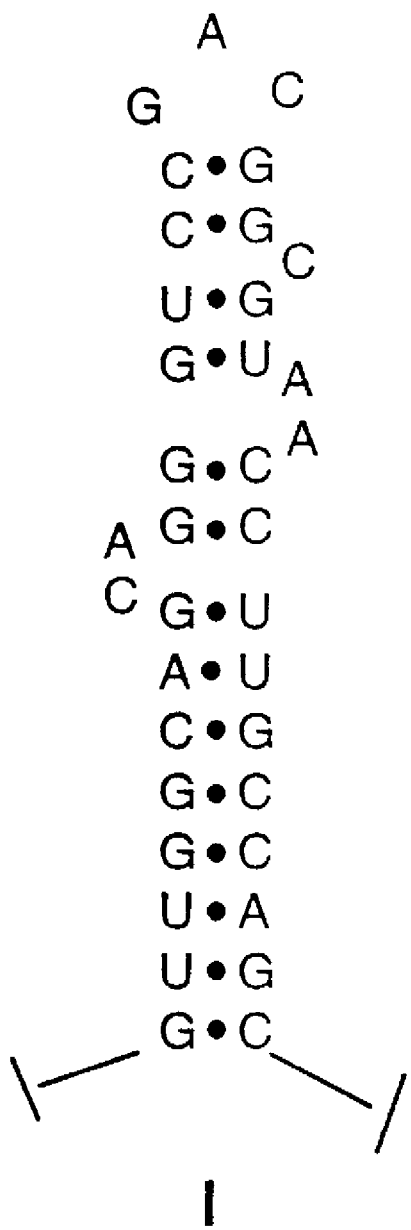
FIG. 2 shows a possible stem-loop structure that can be assumed by ligand T-15 (a fragment of ligand 15, SEQ ID NO:43).

A possible stem-loop structure that can be assumed by ligand T-15 is shown in FIG. 2. Alternatively, if one considers participation of the 5'-fixed region (as is the case for hCG ligands), the T-15 sequence can potentially form an intramolecular G-quartet with two G-planes. Ligand T-15 was therefore tested for RNase T1 protection under the conditions employed for hCG ligands. In contrast to the altered cleavage pattern observed with the hCG ligands, the RNase T1 cleavage patterns observed with ligand T-15 were essentially identical in all three buffers (in urea, KCl, or LiCl), suggesting that ligand T-15 may not fold into a G-quartet structure, in spite of the presence of five guanine doublets in the sequence. These data additionally serve as a good negative control for the RNase T1 protection technique for the identification of G-quartet formation. Thus, T-15 may exist as either a stem-loop structure or a single-stranded form.

EXAMPLE 4.

EXPERIMENTAL PROCEDURES FOR 2'-F-MODIFIED LIGANDS TO hCG

Materials.

Single-stranded DNAs (ssDNA) were obtained from Operon Technologies, Inc. (Alameda, Calif.). Human chorionic gonadotropin (hCG; iodination grade, 14,000 IU/mg) and human luteinizing hormone (hLH; iodination grade, 10,000 IU/mg) were purchased from Scripp Laboratory (San Diego, Calif.) for preparation of affinity matrices and from Vitro Diagnostics, Inc. (Littleton, Colo.) for binding assays. Nitrocellulose membrane filters (0.2 μm pore size; 25 mm diameter) used in filter-binding experiments and 30,000 MWCO spin filters were purchased from Schleicher and Schuell (Keene, N.H.). All radionucleotides were obtained from NEN Research products (Dupont; Wilmington, Del.). 2'-F-modified CTP and UTP were obtained from United States Biochemical (Cleveland, Ohio).

Polymethyl methacrylate-amino beads (6.1 microns, "amino beads") were purchased from Bangs Laboratories Inc. (Carmel, Ind.). NHS-LC-Biotin was purchased from Pierce (Rockford, Ill.). Streptavidin was obtained from Molecular Probes (Eugene, Oreg.). Non-fat dry milk was purchased form Carnation Co. (Los Angeles, Calif.).

Preparation of hCG and hLH Beads for SELEX.

It was found necessary to prepare hCG beads by attaching biotinylated hCG to streptavidin bound to biotinylated amino beads blocked with milk protein. Polystyrene beads directly coated with hCG had greatly diminished binding capacity for antibodies to the alpha and beta chains when compared with a two antibody sandwich assay. With hCG-biotin-streptavidin-biotin-amino beads antibody staining was comparable to two antibody sandwich assays.

Amino beads, 10% w/v, were first washed (10 volumes PBS+0.1% NaN$_3$, 2×3 volumes PBS+0.1% SDS and 2×3 volumes PBS+0.01% Tween 20) and then suspended to a final concentration of 3% in PBS/Tween 20 containing 1.5 mM NHS-LC-Biotin. After incubating, with mixing, for 1 hour at room temperature the beads were washed 2×with 3 volumes of PBS/Tween 20 and then suspended and stored in PBS+0.1% NaN$_3$+2% non-fat dry milk to block the bead surface and prevent non-specific binding of proteins. The beads, 2.5% w/v, were coated with streptavidin 0.4 mg/mL at room temperature for 2 hours and washed with 5×6 volumes PBS+0.1 NaN$_3$+0.5% BSA and stored as a 2.5% suspension in this buffer. Biotinylation of hCG and hLH was accomplished by incubation of either protein at 1 mg/mL with about 0.1 mM NHS-LC-Biotin for 2 hours at room temperature. Free NHS-LC-Biotin was removed by buffer exchange on a Sephadex™ PD-10 column. The presence of biotin on hCG or hLH was confirmed using polystyrene beads coated with an appropriate antibody to either protein and staining with FITC labeled streptavidin. Comparison of fluorescence intensity with that observed using a FITC labeled second antibody also gave an estimate of the number of biotin molecules per molecule of target protein. The final beads were prepared when excess biotin labeled hCG or hLH was incubated with streptavidin beads (0.5 mg/mL of 2.5% bead suspension) for 2 hours at room temperature. Finally the beads were washed with 2×5 volumes of PBS+ 0.1% $NaN_3$+0.5% BSA and suspended at 2.5% w/v in that buffer.

SELEX.

A synthetic single-stranded DNA (ssDNA) pool was used to generate the double-stranded DNA (dsDNA) template for the initial random sequence RNA population. The ssDNAs contained 40 nt of contiguous random sequence flanked by 5' and 3' defined sequences (Table 9 (SEQ ID NO:64). The defined termini permit the primer hybridization required for PCR and complementary DNA (cDNA) synthesis reactions. The template dsDNAs, synthesized by Taq DNA polymerase, have a T7 RNA polymerase promoter at the 5' end. In vitro transcription of 500 pmoles (1–3×10$^{14}$ unique sequences) of dsDNA with 2'-OH purine and 2'-F pyrimidine ribonucleotide triphosphates provided the initial pool of uniformly [α-$^{32}$P]ATP-labeled 87-nt random sequence RNAs.

RNA and hCG concentrations used for each selection cycle are listed in Table 10. For each selection cycle, uniformly $^{32}$P-labeled RNAs were suspended in 100 µl of binding buffer (20 mM sodium phosphate, 150 mM NaCl, 5 mM KCl, 2 mM $MgCl_2$, and 166 mM urea; pH 6.6), heated at 70° C. for 5 minutes, then cooled to room temperature. For the first selection cycle, the renatured RNA was added to bead-coupled hCG that had been washed with and suspended in binding buffer. The suspension was continually mixed on a revolving platform for one hour at room temperature. The beads were pelleted in a microcentrifuge at 1,300×g for 45 seconds and the supernatant was transferred to a separate tube for quantitation. To remove unbound RNAs, the beads (approximately 1 to 7 µl bed volume) were gently suspended in 50 µl of binding buffer followed by pelleting and removal of the supernatant as described above. The beads were washed with a single 50 µl volume of binding buffer for selection cycles 1–4, two 50 µl volumes for cycles 5–7, and three 50 µl volumes for cycles 8–12. Bound RNAs were extracted by suspending the beads in 200 µl of 7M urea plus 200 µl of phenol followed by heating at 60° C. for 10 minutes. After transferring to room temperature, 100 µl of chloroform and 100 µl of water were added, the suspension was mixed by vortexing, and the aqueous and organic phases were separated by centrifugation in a microcentrifuge. The aqueous phase was transferred to a new tube and the organic phase was back-extracted with 100 µl of $H_2O$. The two aqueous phases were combined with 20 µg of yeast tRNA (carrier) followed by recovery of the RNA by ethanol precipitation. For selection cycles two through twelve, the RNAs were counterselected with bead-coupled hLH prior to selection with bead-coupled hCG. The RNAs were incubated with the hLH beads for one hour followed by pelleting of the beads by centrifugation as described above. The supernatant was transferred to bead-coupled hCG; binding and recovery of bound RNAs proceeded as described for selection cycle one.

Reverse transcription and PCR amplification of the cDNAs was accomplished with Tth DNA polymerase as follows: the RNA was included in a 100-µl reverse transcription reaction consisting of 0.2 mM of each dNTP, 100 pmoles of 3p8 oligonucleotide primer (Table 9 SEQ ID NO:66), 0.85 mM $MnCl_2$, 90 mM KCl, 10 mM Tris-HCl, pH 8.3, and 16 units of Tth DNA polymerase. The reaction was incubated at 60° C. for 15 minutes. For PCR amplification of the cDNAs, 100 µl of a Tth reaction solution, containing 0.2 mM dNTPs, 300 pmoles 5p8 primer (Table 9, SEQ ID NO:65), 200 pmoles 3p8 primer, 0.85 mM $MnCl_2$, 90 mM KCl, 10 mM Tris-HCl, pH 8.3, and 8 units of Tth DNA polymerase, was added directly to the cDNA reaction. PCR parameters were 10 to 14 thermal cycles, with each cycle being 45 seconds at 94° C. followed by 45 seconds at 60° C. PCR products were retained on 30,000 molecular weight cut-off (MWCO) microcentrifuge spin filters, washed with 400 µl of water, and finally suspended in 100 µl of water. To produce an enriched RNA pool for the next cycle of selection and amplification, PCR products (50 µl) served as template in a 200-µl transcription reaction that consisted of 1 mM GTP, 1 mM ATP, 3 mM 2'-F-CTP, 3 mM 2'-F-UTP, 80 µCi [α-$^{32}$P]ATP (800 Ci/mmole), 600 units T7 RNA polymerase, and T7 polymerase buffer (40 mM Tris-HCl, pH 8.0, 12 mM $MgCl_2$, 1 mM spermidine, 5 mM DTT, 4% glycerol, 0.002% Triton X-100).

Partitioning of soluble hCG-bound RNAs from unbound RNAs by nitrocellulose filter binding for binding assays and SELEX cycles 13–16 was accomplished by suctioning binding reactions through pre-wet (with binding buffer) filters. After a wash with 5 mL of binding buffer, the filters were either dried and counted (for binding assays) or the bound RNAs were recovered by the extraction procedure described above for RNAs bound to bead-coupled hCG. Table 10 shows the percentage of RNA included in the binding reactions with soluble hCG (at the indicated hCG concentrations) that was retained on the filters. The RNAs from the cycle 13 700 nM hCG binding reaction were recovered and amplified for use in cycle 14. RNAs from the cycle 14 350 nM hCG binding reaction were recovered and amplified for use in cycle 15. RNAs from the cycle 15 150 nM hCG binding reaction were recovered and amplified for use in cycle 16. RNAs from the cycle 16 150 nM binding reaction were recovered, amplified, cloned and sequenced as described supra.

The reverse transcription and PCR amplification of RNAs isolated from the 16th cycle of selection was performed with oligonucleotide primers that contained terminal Bam HI (3p8V (SEQ ID NO:68)) and Hind III (5p8V (SEQ ID NO:67)) restriction endonuclease sites (Table 9). Gel-purified PCR products were cloned into the Bam HI and Hind III sites of pUC18 and sequenced by the dideoxynucleotide termination method using modified T7 DNA polymerase (Sequenase 2.0; United States Biochemical) and universal forward or reverse primers.

DETERMINATION OF EQUILIBRIUM DISSOCIATION CONSTANTS ($K_d$).

Equilibrium dissociation constants ($K_d$ values) were calculated from the relationship (Irvine et al. (1991) J. Mol. Biol. 222:739–761):

$$q=(f/2R_t)\{P_t+R_t+K_d-[(P_t+R_t+K_d)^2-4P_tR_t]^{1/2}\} \qquad (1)$$

(Rifkin and Moscatelli (1989) J. Cell Biol. 109:1–6), where q is the fraction of bound RNA at equilibrium, $P_t$ and $R_t$ are total hCG and total RNA concentrations, and f reflects the efficiency of retention of the protein-RNA complexes on nitrocellulose filters. Data sets that define the binding curves were fit to the equation by the nonlinear least-squares method using the software package KALEIDAGRAPH (Synergy Software, Reading, Pa.).

EXAMPLE 5.

Selection of 2'-F-modified RNA Ligands for hCG

2'-F RNA ligands that bind tightly to hCG were isolated through 12 cycles of selection with bead-coupled hCG followed by four cycles of nitrocellulose filter binding selection with soluble hCG as described in Example 4. Filter binding partitioning was included to remove putative ligands that require interactions with components of the beads other than hCG for high affinity binding. In selection cycles two through twelve, ligands that were capable of binding to the structurally-related glycoprotein hormone hLH were removed from the population by subjecting the RNAs to a counterselection step with bead-coupled hLH prior to addition to the hCG beads. Due to the low concentration of hCG coupled to the beads, the percentage of the input RNA that remained bound to hCG never exceeded 1% (Table 10). Therefore, the improvement in binding of the RNA population to hCG was monitored by nitrocellulose filter binding with soluble hCG. The unselected random sequence RNA pool bound very weakly to hCG in the binding buffer utilized for the SELEX experiments. Virtually no binding (<1%) was observed on nitrocellulose filters at hCG concentrations as high as 80 $\mu$M (the highest concentration assayed), suggesting that the $K_d$ for the random sequence RNA-hCG interaction is significantly greater than 800 $\mu$M. Significant binding above background became apparent after six cycles of selection and amplification. Attempts at enriching this population with the highest affinity ligands by reducing the hCG concentrations in the later cycles resulted in only a slight improvement in the observed population $K_d$S. It should be noted that reductions in hCG concentration were done by reducing the concentration of hCG-bound beads, not by reducing the local concentration of hCG on the beads. Four subsequent cycles of filter binding selection also resulted in only a slight improvement in affinity.

A binding assay was performed to determine the affinity of the cycle 16 RNA population for hCG and hLH. The RNA population exhibited a $K_d$ of approximately 500 nM for hCG. Ligands within these populations can clearly discriminate between hCG and hLH. A comparison of the cycle 16 population with the unselected random RNA population revealed a greater than three-orders of magnitude improvement in affinity for hCG.

Figure 3B:
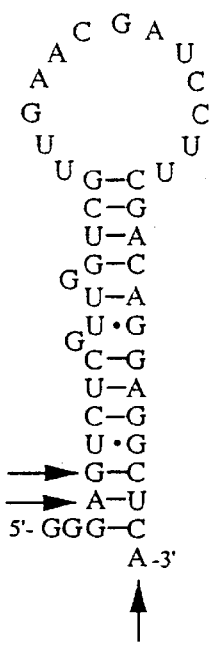
FIG. 3B shows the minimal sequence of hCG ligand 9 required for high affinity binding to hCG (truncated hCG ligand 9TR1 (SEQ ID NO:117)). The nucleotide abbreviations C and U are the modified nucleotides 2'-F-C and 2'-F-U.
Figure 3A:
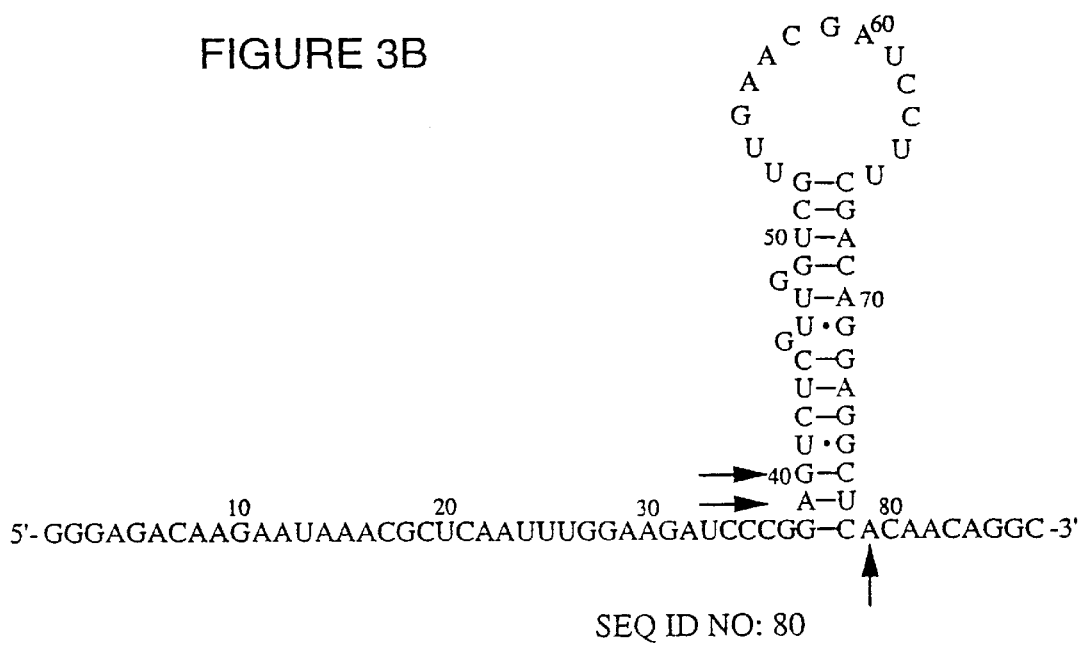
FIG. 3A shows a possible stem loop structure that can be assumed by hCG ligand 9 (SEQ ID NO:80)

PCR products generated from the RNA population resulting after 16 cycles of selection and amplification were cloned into pUC18 and sequenced. The 47 ligand sequences obtained can be placed into two major classes on the basis of functional similarities (Table 11). All members of Class 1 share a highly conserved 13nt sequence (5'-UUGAACGAUCCUU-3') (SEQ ID NO:39). Class 1 members are further divided into two groups on the basis of the location of this conserved sequence. For some members of Class 1, group 1, one or two of the 3'-terminal nucleotides of this sequence belongs to the 3' fixed sequence primer binding site. Only ligands 29 (SEQ ID NO:96), 33 (SEQ ID NO:88), and 41 (SEQ ID NO:104) have nucleotide substitutions or deletions within the conserved sequence. As illustrated in FIG. 3A with ligand 9 (SEQ ID NO:80), all Class 1 ligands can potentially assume a stem-loop structure that places the conserved sequence in the "loop" of this structure. In all cases, formation of the stem involves base-pairing of nucleotides from the 3' (group 1) or 5' (group 2) fixed sequence with selected sequences. Sequences assigned to Class 2 lack the conserved 13nt sequence. Nitrocellulose filter binding assays, using 100 nM hCG and no hCG, were performed in duplicate for each ligand as an initial screen for the highest affinity ligands (Table 11). All Class 2 members exhibited a high affinity for nitrocellulose filters with up to 60% of the RNA bound to the filters in the absence of hCG; a significantly lower percentage of the RNA bound to the filters in the presence of 100 nM hCG. Six-point binding curves for representative "high" and "low" affinity ligands from Class 1 (ligands 6 (SEQ ID NO:85), 9 (SEQ ID NO:80), 19 (SEQ ID NO:94), 25 (SEQ ID NO:102), 33 (SEQ ID NO:88), 36 (SEQ ID NO:100), and 41 (SEQ ID NO:104)) with hCG concentrations ranging from 75 nM to 5 $\mu$M were subsequently performed. The measured $K_d$ values for these ligands are between 150 and 600 nM (data not shown). The highest affinity ligand, represented by ligand 9, was also the most predominant; five of the 47 clones sequenced share this 40-nt selected sequence. Other members of Class 1, Group 1, differ from this sequence at only one to five nucleotide positions suggesting that they are the result of point mutations introduced by the polymerases during the SELEX experiment. The $K_d$ values for the ligand 9-hCG interaction in the selection buffer and in urine (pre-filtered through a 0.45 $\mu$m pore size cellulose acetate membrane), as measured by filter binding, are approximately 155 nM and 75 nM, respectively. The affinity of ligand 9 for hLH is about 250-fold lower (data not shown). hCG Binding analyses by surface plasmon resonance with a BIAcore apparatus provided similar results (data not shown).

Toward the development of an hCG diagnostic assay, the effect of pH on the affinity of ligand 9 for hCG and hLH was determined. Affinity for both hCG and hLH was seen to increase as pH decreased. Very high specificity for hCG is observed at pH values above 6.5.

EXAMPLE 6.

INFORMATION BOUNDARY DETERMINATION FOR LIGAND U9

The 5' and 3' boundaries of the minimal ligand 9 sequence (FIG. 3A, SEQ ID NO:80) required for binding to hCG was determined by identifying the smallest RNA fragment, resulting from partial alkaline hydrolysis, capable of binding to hCG. Gel-purified 5' or 3' $^{32}$P-end-labeled ligand 9 was partially hydrolyzed by incubation at 90° C. for 10 minutes in a 20-$\mu$l reaction containing 0.5 $\mu$g of yeast tRNA, 1 mM EDTA, and 50 mM $Na_2CO_3$ at pH 9.0. Following this incubation, 5 $\mu$l of 100 mM Tris-HCl/1 mM EDTA, pH 7.2, was added. The RNAs were recovered by ethanol precipitation, washed with 70% ethanol, and suspended in 20 $\mu$l of water. Approximately 10 pmoles of partially hydrolyzed RNA was combined with either 100, 200, or 400 nM hCG in 100-$\mu$l binding reactions. After incubation at room temperature for 10 minutes, bound RNAs were partitioned from unbound RNAs by nitrocellulose filter binding, washed with 5 mL of binding buffer, and recovered from the filters, all as described above. Recovered RNAs were separated on an 8% sequencing gel alongside partial alkaline hydrolysis and RNase T1 digest fragment ladders as sequence markers. RNase T1 digest reactions contained approximately 20 pmoles of 5'- or 3'-end-labeled RNA and 5 units of RNase T1 in 10 $\mu$l of T1 buffer (7M urea, 1 mM EDTA, and 20 mM $Na_3$Citrate, pH 5.0) and were incubated at 55° C. for 15 minutes.

The results indicate that the smallest 5' end-labeled fragment with significant affinity for hCG has a residue $A_{79}$ 3' terminus (FIG. 3A). Residue $A_{39}$ or $G_{40}$ is at the 5' terminus of the smallest high affinity 3' end-labeled fragment. Due to the resistance of 2'-F-modified pyrimidines to alkaline hydrolysis, the absence of fragments in the binding reactions that terminate with either a U or C residue prevents the precise localization of the boundaries; the possibility of high affinity fragments with $C_{76}$–$C_{78}$ at the 3' boundary, and $U_{41}$–$C_{44}$ at the 5' boundary cannot be excluded by this experiment.

Based on the information boundary results, a truncated 2'-F RNA ligand (FIG. 3B; 9TR1 (SEQ ID NO:117)) was synthesized as follows: A ssDNA template (Table 9; 9TR1 (SEQ ID NO:69) for the truncated 2'-F RNA ligand was chemically synthesized and PCR amplified using oligonucleotides 5pTR (SEQ ID NO:70) and 3pTR (SEQ ID NO:71) as primers (Table 9). 9TR1 2'-F RNA ligand transcripts generated from the resulting dsDNA templates by T7 RNA polymerase consist of the ligand 9 sequence between and including A38 and A79, with an additional three G residues at the 5' terminus (required for reasonably efficient transcription). The affinity and specificity of ligand 9TR1 for hCG is similar to that seen with the full length ligand in either SBB ($K_d$=200 nM for hCG, >80 $\mu$M for hLH) or urine ($K_d$=100 nM for hCG, >80 $\mu$M for hLH), confirming the information boundary assignments.

EXAMPLE 7.

PARTIAL RANDOMIZATION OF A CONSENSUS hCG LIGAND AND ITS USE IN A "SECOND GENERATION" SELEX

A synthetic ssDNA pool consisting of the conserved 13-nt sequence selected in the initial SELEX flanked on each side by 13 nt of contiguous random sequence and fixed primer binding sites was used as the starting material for a "second generation" SELEX (CG2N7 (SEQ ID NO:76)) (Table 9). Oligonucleotide primers 5p7 (SEQ ID NO:77) and 3p7 (SEQ ID NO:78) (Table 9) were used for the amplification of CG2N7 templates. The bead-coupled hCG selection and hLH counterselection SELEX parameters are summarized in Table 12. The improvement in binding to hCG was more accurately monitored by nitrocellulose filter binding with soluble hCG. Less than 1% of the unselected random RNA bound to hCG at concentrations up to 40 $\mu$M. High affinity binding to hCG was observed after three cycles of selection (population $K_d$ of ~300 nM). The affinity of the RNA population for hCG improved to a $K_d$ of approximately 240 nM after six cycles of selection, without further improvement in selection cycles seven and eight. As in the initial SELEX experiment, the affinity of the RNA population for hLH remained approximately 250-fold lower than that for hCG.

PCR products generated from the RNA population isolated after six cycles of selection were cloned into pUC18 and 43 clones were sequenced (Table 13). As with the high affinity ligands selected in the first SELEX experiment in this example, 37 of the sequenced ligands are capable of assuming a stem-loop structure which places the conserved, unselected, 13-nt sequence in the "loop" structure. No significant base-pairing was observed between the selected sequences in ligands 55 (SEQ ID NO:155), 76 (SEQ ID NO:145), 77 (SEQ ID NO:157), 81 (SEQ ID NO:158), 82 (SEQ ID NO:159) or 97 (SEQ ID NO:160). As an initial screen for the highest affinity ligands, three-point binding curves (50, 100, and 200 nM hCG and a no protein control) were performed with each ligand. Results for binding at 100 nM hCG are shown in Table 13. Complete binding curves with hCG concentrations ranging from 39 nM to 2.5 $\mu$M were performed with the highest affinity ligands (ligands 14 (SEQ ID NO:124), 18 (SEQ ID NO:119), 23 (SEQ ID NO:125), 49 (SEQ ID NO:138), 61 (SEQ ID NO:141), 69 (SEQ ID NO:126), 98 (SEQ ID NO:154)). Ligand 18 exhibited the highest affinity for hCG with a $K_d$ of 150 nM, essentially the same affinity observed for the highest affinity ligand from the first SELEX experiment (ligand 9 (SEQ ID NO:80)).

EXAMPLE 8.

CONSTRUCTION OF LIGAND 25/9 DIMER

Figure 4:
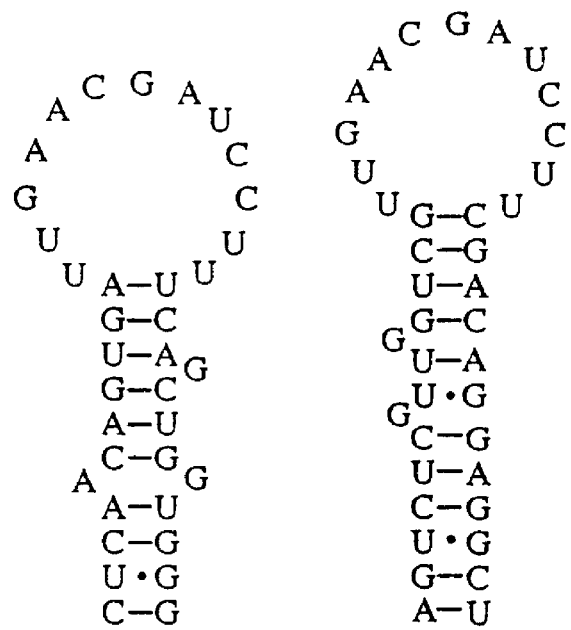
FIG. 4 illustrates the structure of hCG ligand dimer, ligand 25/9 (SEQ ID NO:41). The nucleotide abbreviations C and U are the modified nucleotides 2'-F-G and 2'-F-U.

Template DNA for an hCG ligand dimer (ligand 25/9 (SEQ ID NO:41); FIG. 4) was constructed by annealing oligonucleotides 25DIMR-A (SEQ ID NO:72) and 9DIMR-B (SEQ ID NO:73) to 25/9BRDG (SEQ ID NO:74) (Table 9) followed by ligation of the "A" and "B" oligonucleotides with T4 DNA ligase. This reaction consisted of 500 pmoles 25DIMR-A, 500 pmoles 9DIMR-B, 600 pmoles 25/9BRDG, and 2.5 units T4 DNA ligase in 50 $\mu$l of 1X DNA ligase buffer (supplied with enzyme from New England Biolabs). Following incubation at 37° C. for 2 hours, the ligated oligonucleotides were purified on an 8% denaturing polyacrylamide gel and recovered. Approximately 5 pmoles of the isolated ssDNA dimer template was PCR amplified using Taq DNA polymerase and oligonucleotides 5p8 (SEQ ID NO:65) and 3pDIMR (SEQ ID NO:75) (Table 9) as primers. Ligand 25/9 (FIG. 4, SEQ ID NO:41), transcribed from the dsDNA PCR products with T7 RNA polymerase, consists of the first 59 nucleotides of ligand 25 (SEQ ID NO:102) followed by nucleotide positions 33 to 79 of ligand 9 (SEQ ID NO:80) (Table 11). The affinity of ligand 25/9 for hCG (approximately 200 nM), as determined by nitrocellulose filter binding, was essentially the same as that seen for ligands 9 and 9TR1 (SEQ ID NO:117) alone.

TABLE 1

| Oligonucleotides used to select 2'-NH$_2$RNA ligands to hCG and hTSH |  |
|---|---|
| 40N template oligonucleotide: |  |
| 5'- GGGAGGACGATGCGG-(40N)-CAGACGACTCGCCCGA -3' | SEQ ID NO: 1 |
| PCR primers: |  |
| 5'- GTAATACGACTCACTATAGGGAGGACGATGCGG -3' | SEQ ID NO:2 |
| 5'- TCGGGCGAGTCGTCTG -3' | SEQ ID NO:3 |

TABLE 2

2'-NH$_2$-Modified RNA Ligands to hCG[a]

| Clone Number: | | | | SEQ ID NO: |
|---|---|---|---|---|
| | 5'- GGGAGGACGAUGCGG-(40N)-CAGACGACUCGCCCGA -3' | | | 33 |

Class I:

| Clone | Sequence | SEQ ID NO |
|---|---|---|
| 40(5): | A–UGGGU–GCAGA– U---GCGGU–GGGCAC---GUGGAGGGGA –GCGUAC | 4 |
| 42 : | ACAAGGGCCUGAG– U--GUGGA–GGGCAC---GUGGAGGGGA –CUGGC | 5 |
| 27(2): | UACCA--- U---GUGGA–GGGAAC---GUGGAGGGGU –GUAUGUCAUACCG | 6 |
| 30 : | UACUGUAAAACAA-- U--CUGGA–GGAGG---GUCUAGGGGA –UGGUGG | 7 |
| 49 : | CA–GGUAACGAAGG– AGGGAGGA–GGGUA---GGGACGGGAC –UGGC | 8 |
| 50 : | UACCA--- U---GUGGAAGGGAAC---GUGGAGGGCU –UAUGUCAUACCG | 9 |
| 5 : | CA–CGAGGCU-- A--GUGGA–GGGUAGCAGUGGAGGGGU –AGUGC | 10 |
| 35(3): | AGUGGAUGGC– A--GUGGA–GGGUAC---GAGGAGGGGC –CCACUCUG | 11 |
| 11 : | CCCGAAUC– U---GUGGC–GGGUAC---GUGGAGGGGU –CACU | 12 |
| 15 : | ACUGGAUCGC– A--GUGGA–GGGUAC---GAGGAGGGGC –CCACUCUC | 13 |
| 19 : | AAUGAGCUUAACG– A--GAGGAUGGGUACCAGUGGAGGGGU | 14 |
| 33(2): | CACGAGGCU– A--GUGGA–GGGUAGCAGUGGAGGGGU –AGGCUGC | 15 |
| 46 : | CGAUGCACCUA– U--GAGGA–GGGCAC---GCGGACGGGA –CUGGC | 16 |

Conserved Sequence I: U/A --G A/U GGA–GGGUAC---GUGGAGGGG U/A   17

Class II:

| Clone | Sequence | SEQ ID NO |
|---|---|---|
| 9 : | UGGGUAGCAGUGGAGGGGU –UCAGUCCUCUUUCUGAAGCUG | 18 |
| 17 : | AGGGAAC--GCGGAGGGGU –GUGUCCCCAGACUACAAGGCGG | 19 |
| 21 : | AGGGUAC--GCGGAGGGGA –UAAGUCCUCAGCCACAGUCCCUG | 20 |
| 26 : | AGGGAAC--GCGGAGGGGA –AGCGCCACCCAGAGUUCGGCUG | 21 |
| 36 : | AGGGAAC--GCGGAGGGGA –AGCGCCACCCAGAGGUUCGGCUG | 22 |
| 37(3): | UGGGAAC--GCGGAGGGGA –ACGUCCUCACAGCAAUCCACGC | 23 |
| 53 : | AGGGUAC--GCGGAGGGGU –GUGUCCCCAGACUACAAGGCGG | 24 |

Conserved Sequence II: A/U GGG A/U AC--GCGGAGGGG U/A   25

Class III:

| Clone | Sequence | SEQ ID NO |
|---|---|---|
| 48(2): | CAUAGAAAUAGGAGGAGAA–GGAAGGCUAG–CCCGCACGCCC | 26 |
| 25(4): | AAAGGAGGAGGCUGGGUGCGUCA–AGAGUUCUCCCGAGCGC | 27 |
| 32 : | UCAGACGAGGAUGGGCUGGUAGCGAG–GUAGUGGCUGAGGGG | 28 |
| 34 : | GUAGACGCGGGAGGAGGGUGGACGCAGCG–GACCGAACC | 29 |
| 44 : | AAAGGAGGAGGCUGGGUGAGUCA–AGAGUUCUCCCGAGCGC | 30 | a. Nucleotide Abbreviations C and U are the modified nucleotides 2'—NH$_2$—C and 2'—NH$_2$—U

TABLE 3

Dissociation Constants (K$_d$'s) For a Representative Set of High Affinity RNA Ligands to hCG

| | | K$_d$ (nM) | | | |
|---|---|---|---|---|---|
| Class | Clone Number | hCG | hLH | hFSH | hTSH |
| I | 27 | 44 | | | |
| | 30 | 20 | 51 | ~1700 | ~1600 |
| | 42 | 6.2 | 15 | | |
| II | 17 | 7.5 | | | |
| | 21 | 22 | | | |
| | 35 | 3.9 | 9.5 | >2000 | ~1700 |
| | 26 | 22 | | | |
| III | 25 | 6 | 17.5 | | |
| | 32 | 24 | | | |
| | 44 | 14 | 57 | >2000 | ~1800 |
| | 48 | 20 | | | |

TABLE 4

Fragments of hCG RNA

Ligand H-25(SEQ ID NO:27)Used in Boundary Analysis

\*
5'-GGAAAGGAGGAGGCUGGGUGCGUCAAGAGUCUCCCGAGC-3'

TABLE 5

Dissociation Constants ($K_d$'s) of truncated RNA Ligands to hCG.[a]

| Class | Truncated Sequence (5'-3') | $K_d$ (nM) | SEQ ID NO |
|---|---|---|---|
| II Δ17 | *GGAGGACGAUGCGG*AGGGAACGCGGAGGGGUG[b] | 25 ± 13 (7.5 ± 3) | 35 |
| III Δ25 | *GGAGGACGAUGCGG*AAAGGAGGAGGCUGGGUGCGUC[b] | 24 ± 9 (5.8 ± 2.8) | 34 |

[a]Nucleotide abbreviations C and U are the modified nucleotides 2'-NH$_2$—C and 2'-NH$_2$—U
[b]Italicized type represents fixed sequences.

TABLE 6

H-30  5'-GGAGGACGAUGCGGUACUGUAAAACAAUCUGGGAGAGGGGUCUAGGGGAUGGUGG—
SEQ ID NO:36                       ΔΔ   Δ  ΔΔΔΔ        ΔΔΔΔ    ΔΔ  ΔΔ

H-17  5'-GGAGGACGAUGCGGAGGGAACGCGGAGGGGUGUGUCCCCCAGACUACAAGGCGG—
         ΔΔ  ΔΔ         ΔΔ  ΔΔΔ       ΔΔ  ΔΔΔΔ
SEQ ID NO:37

H-25  5'-GGAGGACGAUGCGGAAAGGAGGAGGCUGGGUGCGUCAAGAGUUCUCCCGAGCGC—
         ΔΔ  ΔΔ       ΔΔ    ΔΔ ΔΔ ΔΔ   ΔΔΔ
SEQ ID NO:38 a. nucleotide abbreviations C and U are the modified nucleotides 2'—NH$_2$—C and 2'—NH$_2$—U
Δ. Indicates Guanines that become protected in KCl buffer

TABLE 7

2'—NH$_2$ modified RNA Lignads to hTSH[a]

| Clone Number | 5'-GGGAGGACGAUGCGG(40N)CAGACGACUCGCCCGA-3' | | | SEQ ID NO: |
|---|---|---|---|---|
| | | | | 33 |
| 26 : | CGUG- | GGGGGGUCU | -GUCCUUUUCACUAGAAGUGACUCUUC | 42 |
| 15(6) : | AUGUUGGCA- | GCAGGGUCC | -DACGGCGUAACCUUGCCAGCUG | 43 |
| 22 : | AUGUUGGCA- | GCAGGGUCC | -GACGGCGUAACCUUGCCGACUG | 44 |
| 1 : | GUACGUAUGGCACAAUUAGGA- | GGAGGCUGU | -GGGGUGAUGG | 45 |
| 4(2) : | GUGGCUUCAGAG- | GGAGGAACG | -GAAGAGGCAAAACCACAGC | 46 |
| 5 : | GUGGCCUCAGAG- | GGAGGAACG | -AGAGCAGCUCAGCCAGGGC | 47 |
| 25 : | GUGGCUUCAGAG- | GGUGGAACG | -AGAGCAGCUCAGCUCAGCC | 48 |
| 23 : | GUGGCUUCAGAG- | GGUGGAACG | -AGAGCAGCUCAGCCAGCC | 49 |
| 8 : | GAGGUCAGUG- | GGUGGAAAC | -GAAGCUGCAGGACUCGCGCUG | 50 |
| 13 : | CCAUGAGGCGAGUG- | GGAGGGAGG | -UUGAAGCGCACGAUUGG | 51 |
| 18 : | GAGGUCAGAG- | GGUGGCACC | -GAAAAGAAAGGAGUUCGCCCC | 52 |
| 19 : | UUUGAGGAGCG- | GGUGGGUGG | -AACGCAGGAGUCAG | 53 |
| 35 : | CACGUAGAGCUAGU- | GGAGGGUAG | -UAGUACACAACUAAAUA | 54 |
| 36(3) : | UUUGAGGAGCG- | GGUGGGUGG | AACGCAGGAGUAGUCCGC | 55 |
| 41(4) : | GUACGUAUGGCACAAUUAGGA- | GGAGGCUCU | -GGGGUGUUGG | 56 |
| 6 : | AGGCU- | GGAGGGUGG | -AGGGAUGCAUGCAGUAUACCGCACCG | 57 |
| 29 : | AAUCACAUGU- | GGUGGGUAC | -GU---GGAGGGGA-AAUUGCCGCC | 58 |
| 27 : | CACGAGGCUAGU- | GGAGGGUAG | -CAGU-GGAGGGUA-CUGC | 59 |
| 7 : | CACGAGGCUAGU- | GGAGGGUAG | -CAGU-GGAGGGGU-ACGCUGC | 60 |
| 10 : | AAUCACAUGU- | GGAGGGUAC | -GU---GGAGGGGA-AAUGGUGACCG | 61 |
| 49 : | CACGAGGCUAGU- | GGAGGGUAG | -CAGU-GGAGGGGU-AGUGC | 62 |
| 50 : | AAUCACAUGU- | GGUGGGUAC | -GU---GGAGGGGA-AUGCGACC | 63 |

TABLE 8

Dissociation Constants ($K_d$'s) of Ligand T-15 (SEQ ID NO: 43)

| Protein | $K_d$ (nM) |
|---|---|
| hTSH | 14 |
| hLH | >1000 |
| hCG | nd |
| hFSH | ~200 |
| α-subunit | >3600 |
| β-subunit (hTSH) | >3200 |

TABLE 9

Oligonucleotides used in the Generation of 2'-F-Modified Ligands to hCG
OLIGONUCLEOTIDES (5' TO 3')

| | | SEQ ID NO: |
|---|---|---|
| 40N8: | GGGAGACAAGAATAAACGCTCAA-$N_{40}$-TTCGACAGGAGGCTCACAACAGGC | 64 |
| 5p8: | TAATACGACTCACTATAGGGAGACAAGAATAAACGCTCAA | 65 |
| 3p8: | GCCTGTTGTGAGCCTCCTGTCGAA | 66 |
| 5p8V: | CAGAAGCTTAATACGACTCACTATAGGGAGACAAGAATAAACGCTCAA | 67 |
| 3p8V: | GACTGGATCCGCCTGTTGTGAGCCTCCTGTCGAA | 68 |
| 9TR1: | TAATACGACTCACTATAGGGAGTCTCGTTGGTCGTTGAACGATCCTTCGACAGGAGGCTCA | 69 |
| 5pTR: | TAATACGACTCACTATAG | 70 |
| 3pTR: | TGAGCCTCCTGTCGAAGGATC | 71 |
| 25DIMR-A | GGGAGACAAGAATAAACGCTCAACAGTGATTGAACGATCCTTTCAGCTGGTGGGTA | 72 |
| 9DIMR-B | TGGTCCCGGAGTCTCGTTGGTCGTTGAACGATCCTTCGACAGGAGGCTCA | 73 |
| 25/9BRDG | CCGGGACCATACCCACCA | 74 |
| 3pDIMR | TGAGCCTCCTGTCGAAGG | 75 |
| CG2N7 | GGGAGGACGATGCG-$N_{13}$-TTGAACGATCCTT-$N_{13}$-CAGACGACTCGCCCGA | 76 |
| 5p7 | TAATACGACTCACTATAGGGAGGACGATGCGG | 77 |
| 3p7 | TCGGGCGAGTCGTCTG | 78 |

TABLE 10

Summary of the SELEX experiment parameters and results for 2'-F-Modified RNA

| Selection cycle | [hLH], nM[a] | [hCG], nM[b] | pmoles RNA | [RNA] | Percent Bound[c] |
|---|---|---|---|---|---|
| 1 | 0 | 48 | 2,500 | 16.5 μM | 0.44 |
| 2 | 96 | 48 | 500 | 3.3 μM | 0.23 |
| 3 | 96 | 28 | 200 | 1.3 μM | 0.07 |
| 4 | 48 | 28 | 50 | 330 nM | 0.13 |
| 5 | 48 | 28 | 50 | 330 nM | 0.20 |
| 6 | 48 | 28 | 50 | 330 nM | 0.35 |
| 7 | 48 | 28 | 50 | 330 nM | 0.62 |
| 8 | 48 | 14 | 50 | 165 nM | 0.47 |
| 9 | 48 | 14 | 50 | 165 nM | 0.76 |
| 11 | 48 | 7 | 50 | 83 nM | 0.17 |
| 12 | 48 | 7 | 50 | 83 nM | 0.32 |

FILTER BINDING[d]:

| Cycle | 700 nM | 350 nM | 150 nM | 75 nM |
|---|---|---|---|---|
| 13 | 11.4 | 4.1 | 0.0 | |
| 14 | | 13.0 | 0.1 | |
| 15 | | | 7.8 | 2.3 |
| 16 | | | 6.1 | 0.8 |

[a] concentration of hLH used for counterselection. A counterselection step was not included in the first selection cycle.
[b] concentration of hCG used for selection.
[c] the % of the RNA added to the binding reaction that remained bound to the bead-coupled hCG following the binding reaction and wash steps.
[d] summary of results from nitrocellulose filter binding selections 13–16.

TABLE 11

2'-F-Modified RNA Ligands to hCG[a]

5'-GGGAGACAAGAAUAAACGCUCAA—40N—UUCGACAGGAGGCUCACAACAGGC-3'

| Sequence # | | | | Percent Bound 100 nM hCG | SEQ ID NO: |
|---|---|---|---|---|---|
| Class 1: | | | | | |
| Group 1: | | | | | 79 |
| 9,32,34, 44,51 | GGGAGACAAGAAUAAACGCUCAA | UUUGGAAGAUCCCGGAGUCUCGUUGGUCGUUGAACGAUCC | UUCGACAGGAGGCUCACAACAGGC | 5.65 | 80 |
| 4 | GGGAGACAAGAAUAAACGCUCAA | UUUGGAAGAUCCCGGAGUCUCGUUGGU-GUUGAACGAUCC | UUCGACAGGAGGCUCACAACAGGC | 4.81 | 81 |
| 11 | GGGAGACAAGAAUAAACGCUCAA | UUUAGAAGAUCCCGGAGUCUCGUUGGUCGUUGAACGAUCC | UUCGACAGGAGGCUCACAACAGGC | 3.09 | 82 |
| 10 | GGGAGACAAGAAUAAACGCUCAA | UUCGGAAGAUCACGGAGUCUCGUUGGUCGUUGAACGAUCC | UUCGACAGGGGCUCACAACAGGC | 3.59 | 83 |
| 49 | GGGAGACAAGAAUAAACGCUCAA | UUUGGAAGAUCCCGAGAGUCUCGUUGGUCGUUGAACGAUCC | UUCGACAGGAGGCUCACAACAGGC | 3.77 | 84 |
| 1,6,7 | GGGAGACAAGAAUAAACGCUCAA | UUUGGAAGAUCCAGAGUCUCGUUGGUCGUUGAACGAUCC | UUCGACAGGAGGCUCACAACAGGC | 4.64 | 85 |
| 16 | GGGAGACAAGAAUAAACGCUCAA | UUCGGAAGAUCCCAGAGUCUCGUUGGUCGUUGAACGAUCC | UUCGACAGGAGGCUCACAACAGGC | 5.41 | 86 |
| 40 | GGGAGACAAGAAUAAACGCUCAA | UUCUGAAGAUCCCAGAGUCUCGUUGGUCGUUGAACGAUCC | UUCGACAGGAGGCUCACAACAGGC | 2.20 | 87 |
| 33 | GGGAGACAAGAAUAAACGCUCAA | UUUGGAAGAUCCCAGAGUCUCGUUGGUCGUUAAACGAUCC | UUCGACAGGAGGCUCACAACAGGC | 0.03 | 88 |
| 26,48,53 | GGGAGACAAGAAUAAACGCUCAA | UUUGGAAGAUCCCUGAGUCUCGUUGGUCGUUGAACGAUCC | UUCGACAGGAGGCUCACAACAGGC | 3.34 | 89 |
| 18 | GGGAGACAAGAAUAAACGCUCAA | UUUCGAAGAUCCCUGAGUCUCGUUGGUCGUUGAACGAUCC | UUCGACAGGAGGCUCACAACAGGC | 2.69 | 90 |
| 56 | GGGAGACAAGAAUAAACGCUCAA | UUUGGAAGAUCCCUGGAGUCUCGUUGGUCGUUGAACGAUCCUUCGACAGGAGGCUCACAACAGGC | | 3.85 | 91 |

TABLE 11-continued

2'-F-Modified RNA Ligands to hCG[a]

| Sequence # | | | Percent Bound 100 nM hCG | SEQ ID NO: |
|---|---|---|---|---|
| 37 | GGGAGACAAGAAUAAACGCUCAA UUUGGAAGGUCC–UGAGUCUCGUUGGUCGUUGAACGAUCC UUCGACAGGAGGCUCACAACAGGC | | 1.89 | 92 |
| 5 | GGGAGACAAGAAUAAACGCUCAA AUUGGAGUAUCCCUGAGUCUGUUGGUCGUUGAACGGUUC UUCGACAGGAGGCUCACAACAGGC | | 1.26 | 93 |
| 19 | GGGAGACAAGAAUAAACGGCUCAA AAGUCCCUCGCAGAGUCUGCUGGUUCGAUUGAACGAUCCU UUCGACAGGAGGCUCACAACAGGC | | 0.84 | 94 |
| 30 | GGGAGACAAGAAUAAACGCUCAA AAGUCACUCGCAGCGCUUCCUGGUUCGAUUGAACGAUCCU UUCGACAGGAGGCUCACAACAGGC | | 0.58 | 95 |
| 29 | GGGAGACAAGAAUAAACGCUCAA AAGCCCUCGCAUAGCUUCCUCGUUCGAUUGAACGAUCCC UUCGACAGGAGGCUCACAACAGGC | | 0.03 | 96 |
| 8 | GGGAGACAAGAAUAAACGCUCAA GUGCCCUGUUAU––CUUCCCGAUCGAUUGAACGAUCCU UUCGACAGGAGGCUCACAACAGGC | | 0.98 | 97 |
| 43 | GGGAGACAAGAAUAAACGCUCAA CCAGAUAAUCCCAAUGAGUCCCUCGAGAUUGAACGAUCCU UUCGACAGGAGGCUCACAACAGGC | | 0.93 | 98 |
| 20 | GGGAGACAAGAAUAAACGCUCAA GUCAUAAGCCUAACGGUCCUAGUCAAUUGAACGAUCC UUCGACAGGAGGCUCACAACAGGC | | 0.13 | 99 |
| Group 2: | | | | |
| 3,36,52 | GGGAGACAAGAAUAAACGCUCAA CAGCGAUUGAACGAUCCUUUCAGCUGAUGGGUAUGGGA UUCGACAGGAGGCUCACAACAGGC | | 0.60 | 100 |
| 28 | GGGAGACAAGAAUAAACGCUCAA ACAGCGAUUGAACGAUCCUUUCAGCUGAUGGGUACGGGA UUCGACAGGAGGCUCACAACAGGC | | 0.58 | 101 |
| 25 | GGGAGACAAGAAUAAACGCUCAA CAGUGAUUGAACGAUCCUUUCAGCUGGUGGGUAUGGGG UUCGACAGGAGGCUCACAACAGGC | | 2.20 | 102 |
| 45 | GGGAGACAAGAAUAAACGCUCAA CAGUGAUUGAACGAUCCUU–CAGCUGAUGGGUAUGGGA UUCGACAGGAGGCUCACAACAGGC | | ND | 103 |
| 41 | GGGAGACAAGAAUAAACGCUCAA CAGCGAUUGAACGA–CCUU–CAGCUGAUGGGUAUGGGA UUCGACAGGAGGCUCACAACAGGC | | 0.61 | 104 |
| Class 2: | | | | |
| 12 | GGGAGACAAGAAUAAACGCUCAA CCAAAGGAGCAUCUGUCGUAUGGGAGGACGAGG–AAGGG UUCGACAGGAGGCUCACAACAGGC | | NEG | 105 |
| 39 | GGGAGACAAGAAUAAACGCUCAA CCAAAGGAGCAUCUGUCGUUAUGGGAGGAUGAGGGAAGGG UUCGACAGGAGGCUCACAACAGGC | | NEG | 106 |
| 38 | GGGAGACAAGAAUAAACGCUCAA CCAAAGGAGCAUCUGUUGUUAUGGGAGGAUGAGGGAAGGG UUCGACAGGAGGCUCACAACAGGC | | NEG | 107 |

TABLE 11-continued

2'-F-Modified RNA Ligands to hCG[a]

| Sequence # | | | Percent Bound 100 nM hCG | SEQ ID NO: |
|---|---|---|---|---|
| 17 | GGGAGACAAGAAUAAACGCUCAA | CCAAUUGAG-AACCGUCGAUGUGGGAGG-GAGGGAGGAA | UUCGACAGGAGGCUCACAACAGGC | NEG | 108 |
| 15 | GGGAGACAAGAAUAAACGCUCAA | UGAGUCAACAAA--GAAAUGGAGGGAGG-AGAGGGAGGAAU | UUCGACAGGAGGCUCACAACAGGC | NEG | 109 |
| 47 | GGGAGACAAGAAUAAACGCUCAA | UGAGCAACCAGA--GAA-UGGAGG-AGG-AGAGGGAGGAAU | UUCGACAGGAGGCUCACAACAGGC | NEG | 110 |
| 54 | GGGAGACAAGAAUAAACGCUCAA | UGAGCCAACCAAAGGAA-UGGAGGGAGG-AGAGGGAGGAGU | UUCGACAGGAGGCUCACAACAGGC | NEG | 111 |
| 23 | GGGAGACAAGAAUAAACGCUCAA | UGAUGGGCUACUCGGGAUCGAAA-GAGGGU--GGGAGGGAGGAUUCGACAGGAGGCUCACAACAGGC | | NEG | 112 |
| 31 | GGGAGACAAGAAUAAACGCUCAA | UGUGAGGGUG----GAAUAGGAGGGAGGUAUUUGAGCUGGAACUUCGACAGGAGGCUCACAACAGGC | | NEG | 113 |
| 21 | GGGAGACAAGAAUAAACGCUCAA | GUGGUAGAUAUGAGGGAA-GGGUGGGAGGCAACACUAGGA | UUCGACAGGAGGCUCACAACAGGC | NEG | 114 |
| 24 | GGGAGACAAGAAUAAACGCUCAA | GAUCGAAGACAACGU---GGGUGGGAGGGAGGUAAAUGUACCUUCGACAGGAGGCUCACAACAGGC | | NEG | 115 |
| 42 | GGGAGACAAGAAUAAACGCUCAA | CAGUGGAGGGAGGUUAUGAGGGGAUGGGAUGUUAAAGCGCAA | UUCGACAGGAGGCUCACAACAGGC | NEG | 116 | a. Nucleotide abbreviations C and U are the modified nucleotides 2'-F—C and 2'-F—U

TABLE 12

Summary of second generation SELEX experiment parameters and results

| Selection cycle | [hLH], nM[a] | [hCG], nM[b] | pmoles RNA | [RNA] | Percent Bound[c] |
|---|---|---|---|---|---|
| 1 | 0 | 72 | 900 | 4.5 μM | 0.04 |
| 2 | 96 | 48 | 300 | 2.0 μM | 0.04 |
| 3 | 96 | 48 | 100 | 667 nM | 0.27 |
| 4 | 24 | 24 | 100 | 333 nM | 0.31 |
| 5 | 24 | 12 | 100 | 333 nM | 0.35 |
| 6 | 24 | 6 | 50 | 83 nM | 0.49 |
| 7 | 24 | 3 | 50 | 42 nM | 0.39 |
| 8 | 0 | 3 | 25 | 21 nM | 0.43 |

[a] Concentration of hLH for counterselection during each selection cycle. A counterselection step was not included in the first selection cycle.
[b] Concentration of hCG used for selection during each cycle. The quantity and concentration of RNA included in each binding reaction are shown.
[c] The percentage of the RNA added to the binding reaction that remained bound to the bead-coupled hCG following the binding reaction and wash steps. The beads (approximately 1 to 7 μl bed volume) were washed with a single 50 μl volume of binding buffer for selection cycles 1–4, two 50 μl volumes for cycles 5–6, and three 50 μl volumes for cycles 7–8.

TABLE 13

2'-F RNA Ligands to hCG[a]

5'-gggaggacgaugcgg-$N_{13}$—UUGAACGAUCCUU—$N_{13}$-cagacgacucgcccga-3'    SEQ ID NO: 40

| Sequence Number | | | | Percent Bound @ 100nM hCG | SEQ ID NO: |
|---|---|---|---|---|---|
| 4 | g g GUUCGACAUAAUC | UUGAACGAUCCUU | GAUUACUUGGUCCc | 13.0 | 118 |
| 18 | g CAUUCGCUGAUUC | UUGAACGAUCCUU | GAUGAUGUGGAUGc | 17.2 | 119 |
| 9 | g g UUCUACACGAUAU | UUGAACGAUCCUU | GUAUCUUAGGUCC | 9.98 | 120 |
| 59 | g g UAACUCUUAAUUC | UUGAACAAUCCUU | GAAUUUAGCGGACc | 1.88 | 121 |
| 72 | g AUUCGAUGUAGU | UUGAACGAUCCUU | GUAUAUAUCGGAUc | 0.30 | 122 |
| 8 | g g UUCGAUUCCAAG | UUGAACGAUCCUC | CUUUUGAUUAGACc | 0.73 | 123 |
| 14 | g g UUCGACACGAAAG | UUGAACGAUCCUU | CUAUCUGUUGGACc | 15.4 | 124 |
| 23 | g GUUUAAUACAAAG | UUGAACGAUCCUU | CUUUGCAUUGGACc | 13.0 | 125 |
| 69 | GUUUCACUUCAAG | UUGAACGAUCCUU | CUUGGCUUGAGCAc | 18.8 | 126 |
| 5 | g GUUUAAUCUCGGA | UUGAACGAUCCUU | UCUGUAAUUAGUCc | 3.14 | 127 |
| 7 | g g AUGAGCUUGAUAA | UGGAACGAUCCUU | UUAACGGUUCUUCc | 0.00 | 128 |
| 10 | AACACCAAUCUUU | UUGAACGAUCCUU | CGUGGGAGUGCAU | 0.00 | 129 |
| 11 | GAUUCUCUUUGAG | UUGAACGAUCCUU | CUCAUCGCACUUGC | 10.0 | 130 |

TABLE 13-continued

2'-F RNA Ligands to hCG[a]

| Sequence Number | | | | Percent Bound @ 100nM hCG | SEQ ID NO: |
|---|---|---|---|---|---|
| 19 | g g UUUGACGUAUAA | UUGAACGAUCCUU | UUCUAGCUUAGACc | 8.52 | 131 |
| 20 | UGUUCAUGCUUGA | UUGAACGAUCCUU | UCAUAGUGUUGGU | 8.37 | 132 |
| 25 | UUCCUGAUUCAAG | UUGAACGAUCCUU | CCUGCUGUACGUC | 0.28 | 133 |
| 28 | g GUUCGAUUUACCU | UUGAACGAUCCUU | ACUUAGCUUCCACc | ND | 134 |
| 33 | g g UUCGAUGGCCAU | UUGAACGAUCCUU | AUUAUCAACGGUCc | 0.59 | 135 |
| 37 | g AAUUCCCCCAAGA | UUGAACGGUCCUU | UCUCGCAGAUGUUc | 0.00 | 136 |
| 42 | g g GUUCGAAACUUCC | UUGAACGAUCCUU | GGAUGUUUUGCUc | 0.54 | 137 |
| 49 | g g UUCGUCAUCGCUA | UUGAACGAUCCUU | UAGCUGAUGGACc | 14.5 | 138 |
| 52 | GAUUUUCCGUUAA | UUGAACGAUCCUU | UUCACGGACUG | 6.01 | 139 |
| 58 | g UCUUAAGUUUGAA | UUGAACGAUCCUU | UUCUUCCAGGCAAc | 0.00 | 140 |
| 61 | g g UUUAGUGUUUAG | UUGAACGAUCCUU | CUAACACCAGUCC | 15.5 | 141 |
| 71 | g AUUCGAUUAGAGA | UUGAACGAUCCUU | UCAUCAGUUGGAUc | 6.99 | 142 |
| 73 | g GGUUUUCUAAGUG | UUGAACGAUCCUU | CACAUAGCGUGUCCc | 0.84 | 143 |
| 74 | g UAAGUUCUAACUU | UUGAACGAUCCUU | GGCACCCUGACUAc | 11.5 | 144 |
| 76 | ACCGACUAAAUGA | UUGAACGAUCCUU | AUUGUCUCUAUCA | 0.20 | 145 |
| 83 | g g UUUGAUGAGGUAG | UUGAACGAUCCUU | CCAUCCGUUAGACc | 4.48 | 146 |
| 84 | UUGGUUAUCCAUG | UUGAACGUUCCUU | CAUGUCGAAUAUGc a g | 0.24 | 147 |
| 86 | g g UUCAACAACGUAC | UUGAACGAUCCUU | GUGCUCGUUGAUC | 0.57 | 148 |
| 88 | g g UUCGUUACGAUAA | UUGAACGAUCCUU | UUAUCUUUCAGUCc | 0.32 | 149 |
| 89 | g UGCAUGAUUUAG | UUGAACGAUCCUU | CCAACUUCCAGCAc | 0.21 | 150 |
| 91 | UUCAUUUUUGUG | UUGAACGAUCCUU | CACUAACCUACCA | 2.36 | 151 |
| 93 | g g UUCUAGGUCGAAA | UUGAACGAUCCUU | UUUCGCUAUGGAUc | 7.25 | 152 |
| 95 | g GUUUUCCUACUAG | UUGAAUGAUCCUU | CUAGUUAGAUGCc | 1.57 | 153 |
| 98 | g g GUUCCAGUAUUAG | UUGAACGAUCCUU | CUUAUCUGGAGUCc | 11.7 | 154 |
| 55 | UUUUACUUAUUUA | UUGAACGAUCCUU | UUUCCCCUAUGCC | BKD | 155 |
| 76 | ACCGACUAAAUGA | UUGAACGAUCCUU | AUUGUCUCUAUCA | 0.20 | 156 |

TABLE 13-continued

2'-F RNA Ligands to hCG[a]

| Sequence Number | Sequence | | | Percent Bound @ 100nM hCG | SEQ ID NO: |
|---|---|---|---|---|---|
| 77 | CAGUGUCAACAUC | UUGAACGAUCCUU | UUUUUCAGCGCGU | 0.42 | 157 |
| 81 | UCAAUCAAGCUUC | UUGAACGAUCCUU | GAUUCGUAACUUC | ND | 158 |
| 82 | UAACAGUCGAUUC | UUGAACGAUCCUU | UCCACUUCAACCG | 0.00 | 159 |
| 97 | UCUUAACCUUUAC | UUGAACGACCCUU | UAUUAGUUUUUCU | BKD | 160 | a) Nucleotide abbreviations C and U are the modified nucleotides 2'-F—C and 2'-F—U. Bold lettering represents mutations in the conserved region. Lowercase letters represent fixed primer binding sequences. Underlining represents possible secondary structure.

We claim:

1. A method of identifying nucleic acid ligands to a Chorionic Gonadotropin (CG)-related glycoprotein hormone, comprising:

a) preparing a candidate mixture of nucleic acids;
   b) contacting the candidate mixture of nucleic acids with a CG-related glycoprotein hormone, wherein nucleic acids having an increased affinity to the CG-related glycoprotein hormone relative to the candidate mixture may be partitioned from the remainder of the candidate mixture;
   c) partitioning the increased affinity nucleic acids from the remainder of the candidate mixture; and
   d) amplifying the increased affinity nucleic acids to yield a mixture of nucleic acids enriched for nucleic acids with relatively higher affinity and specificity for binding to the CG-related glycoprotein hormone, whereby nucleic acid ligands of CG-related glycoprotein hormone may be identified.

2. The method of claim 1 further comprising:
   e) repeating steps b), c), and d).

3. The method of claim 1 further comprising contacting the increased affinity nucleic acids with one or more non-target molecules, wherein nucleic acids with affinity to the non-target molecule(s) are removed.

4. The method of claim 3 wherein the non-target molecule is a member of the CG-related glycoprotein hormone family other than the one for which increased affinity nucleic acids are being selected.

5. A method of identifying nucleic acid ligands to a human Chorionic Gonadotropin (hCG)-related glycoprotein hormone, comprising:

a) preparing a candidate mixture of nucleic acids;
   b) contacting the candidate mixture of nucleic acids with an hCG-related glycoprotein hormone, wherein nucleic acids having an increased affinity to the hCG-related glycoprotein hormone relative to the candidate mixture may be partitioned from the remainder of the candidate mixture;

c) partitioning the increased affinity nucleic acids from the remainder of the candidate mixture; and d) amplifying the increased affinity nucleic acids to yield a mixture of nucleic acids enriched for nucleic acids with relatively higher affinity and specificity for binding to the hCG-related glycoprotein hormone, whereby nucleic acid ligands of hCG-related glycoprotein hormone may be identified.

6. The method of claim 5 further comprising:

e) repeating steps b), c), and d).

7. The method of claim 5 further comprising contacting the increased affinity nucleic acids with one or more non-target molecules, wherein nucleic acids with affinity to the non-target molecule(s) are removed.

8. The method of claim 7 wherein the non-target molecule is a member of the hCG-related glycoprotein hormone family other than the one for which increased affinity nucleic acids are being selected.

9. The method of claim 5 wherein said candidate mixture of nucleic acids is comprised of single stranded nucleic acids.

10. The method of claim 9 wherein said single stranded nucleic acids are ribonucleic acids.

11. The method of claim 10 wherein said nucleic acids are 2'-amino (2'-NH$_2$) modified ribonucleic acids.

12. The method of claim 10 wherein said nucleic acids are 2'-F modified ribonucleic acids.

13. The method of claim 5, wherein said hCG-related glycoprotein hormone is hCG.

14. The method of claim 5, wherein said hCG-related glycoprotein hormone is human thyroid-stimulating hormone (hTSH).

* * * * *

SEQUENCE LISTING ( 1 ) GENERAL INFORMATION:

( i i i ) NUMBER OF SEQUENCES: 160

( 2 ) INFORMATION FOR SEQ ID NO:1:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GGGAGGACGA TGCGGNNNNN NNNNNNNNN NNNNNNNNN NNNNNNNNN 50

NNNNNCAGA CGACTCGCCC GA 72

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GTAATACGAC TCACTATAGG GAGGACGATG CGG 33

( 2 ) INFORMATION FOR SEQ ID NO:3:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TCGGGCGAGT CGTCTG 16

( 2 ) INFORMATION FOR SEQ ID NO:4:

( i ) SEQUENCE CHARACTERISTICS:
        ( A ) LENGTH: 70 base pairs (B) TYPE: nucleic acid
(C) STRANDEDNESS: single
(D) TOPOLOGY: linear (ix) FEATURE:
(D) OTHER INFORMATION: All C's are 2'-NH2 modified (ix) FEATURE:
(D) OTHER INFORMATION: All U's are 2'-NH2 modified (xi) SEQUENCE DESCRIPTION: SEQ ID NO:4:

```
GGGAGGACGA UGCGGAUGGG UGCAGAUGCG GUGGGCACGU GGAGGGGAGC          50
GUACCAGACG ACUCGCCCGA                                           70
```

(2) INFORMATION FOR SEQ ID NO:5:

(i) SEQUENCE CHARACTERISTICS:
(A) LENGTH: 71 base pairs
(B) TYPE: nucleic acid
(C) STRANDEDNESS: single
(D) TOPOLOGY: linear (ix) FEATURE:
(D) OTHER INFORMATION: All C's are 2'-NH2 modified (ix) FEATURE:
(D) OTHER INFORMATION: All U's are 2'-NH2 modified (xi) SEQUENCE DESCRIPTION: SEQ ID NO:5:

```
GGGAGGACGA UGCGGACAAG GGCCUGAGUG UGGAGGGCAC GUGGAGGGGA          50
CUGGCCAGAC GACUCGCCCG A                                         71
```

(2) INFORMATION FOR SEQ ID NO:6:

(i) SEQUENCE CHARACTERISTICS:
(A) LENGTH: 71 base pairs
(B) TYPE: nucleic acid
(C) STRANDEDNESS: single
(D) TOPOLOGY: linear (ix) FEATURE:
(D) OTHER INFORMATION: All C's are 2'-NH2 modified (ix) FEATURE:
(D) OTHER INFORMATION: All U's are 2'-NH2 modified (xi) SEQUENCE DESCRIPTION: SEQ ID NO:6:

```
GGGAGGACGA UGCGGUACCA UGUGGAGGGA ACGUGGAGGG GUGUAUGUCA          50
UACCGCAGACG ACUCGCCCG A                                         71
```

(2) INFORMATION FOR SEQ ID NO:7:

(i) SEQUENCE CHARACTERISTICS:
(A) LENGTH: 71 base pairs
(B) TYPE: nucleic acid
(C) STRANDEDNESS: single
(D) TOPOLOGY: linear (ix) FEATURE:
(D) OTHER INFORMATION: All C's are 2'-NH2 modified (ix) FEATURE:
(D) OTHER INFORMATION: All U's are 2'-NH2 modified (xi) SEQUENCE DESCRIPTION: SEQ ID NO:7:

```
GGGAGGACGA UGCGGUACUG UAAAACAAUC UGGAGGAGGG UCUAGGGGAU          50
GGUGGCAGAC GACUCGCCCG A                                         71
```

( 2 ) INFORMATION FOR SEQ ID NO:8:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:8:

```
GGGAGGACGA UGCGGCAGGU AACGAAGGAG GGAGGAGGGU AGGGACGGGA        50
CUGGCCAGAC GACUCGCCCG A                                        71
```

( 2 ) INFORMATION FOR SEQ ID NO:9:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:9:

```
GGGAGGACGA UGCGGUACCA UGUGGAAGGG AACGUGGAGG GCUUAUGUCA        50
UACCGCAGAC GACUCGCCCG A                                        71
```

( 2 ) INFORMATION FOR SEQ ID NO:10:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:10:

```
GGGAGGACGA UGCGGCACGA GGCUAGUGGA GGGUAGCAGU GGAGGGGUAG        50
UGCCAGACGA CUCGCCGA                                            69
```

( 2 ) INFORMATION FOR SEQ ID NO:11:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:11:

```
GGGAGGACGA UGCGGAGUGG AUCGCAGUGG AGGUACGAG GAGGGGCCCA         50
```

```
CUCUGCAGAC GACUCGCCCG A                                                           71
```

( 2 ) INFORMATION FOR SEQ ID NO:12:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:12:

```
GGGAGGACGA UGCGGCCCGA AUCUGUGGCG GGUACGUGGA GGGGUCACUC         50
AGACGACUCG CCCGA                                               65
```

( 2 ) INFORMATION FOR SEQ ID NO:13:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:13:

```
GGGAGGACGA UGCGGACUGG AUCGCAGUGG AGGGUACGAG GAGGGGCCCA         50
CUCUCCAGAC GACUCGCCCG A                                        71
```

( 2 ) INFORMATION FOR SEQ ID NO:14:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:14:

```
GGGAGGACGA UGCGGAAUGA GUCUUAACGA GAGGAUGGGU ACCAGUGGAG         50
GGGUCAGACG ACUCGCCCGA                                          70
```

( 2 ) INFORMATION FOR SEQ ID NO:15:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:15:

GGGAGGACGA UGCGGCACGA GGCUAGUGGA GGGUAGCAGU GGAGGGGUAG 50

GCUGCCAGAC GACUCGCCCG A 71

( 2 ) INFORMATION FOR SEQ ID NO:16:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:16:

GGGAGGACGA UGCGGCGAUG CACCUAUGAG GAGGGCACGC GGACGGGACU 50

GGCCAGACGA CUCGCCCGA 69

( 2 ) INFORMATION FOR SEQ ID NO:17:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( i x ) FEATURE:
        ( B ) LOCATION: 1, 3, 22
        ( D ) OTHER INFORMATION: N is U/A ( x i ) SEQUENCE DESCRIPTION: SEQ ID NO:17:

NGNGGAGGGU ACGUGGAGGG GN 22

( 2 ) INFORMATION FOR SEQ ID NO:18:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:18:

GGGAGGACGA UGCGGUGGGU AGCAGUGGAG GGGUUCAGUC CUCUUUCUGA 50

AGCUGCAGAC GACUCGCCCG A 71

( 2 ) INFORMATION FOR SEQ ID NO:19:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:19:

GGGAGGACGA UGCGGAGGGA ACGCGGAGGG GUGUGUCCCC CAGACUACAA     50

GGCGGCAGAC GACUCGCCCG A     71

( 2 ) INFORMATION FOR SEQ ID NO:20:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:20:

GGGAGGACGA UGCGGAGGGU ACGCGGAGGG GAUAAGUCCU CAGCCACAGU     50

CCCUGCAGAC GACUCGCCCG A     71

( 2 ) INFORMATION FOR SEQ ID NO:21:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:21:

GGGAGGACGA UGCGGAGGGA ACGCGGAGGG GAAGCGCCAC CCAGAGUUCG     50

GCUGCAGACG ACUCGCCCGA     70

( 2 ) INFORMATION FOR SEQ ID NO:22:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:22:

GGGAGGACGA UGCGGAGGGA ACGCGGAGGG GAAGCGCCAC CCAGAGGUUC     50

GGCUGCAGAC GACUCGCCCG A     71

( 2 ) INFORMATION FOR SEQ ID NO:23:

( i ) SEQUENCE CHARACTERISTICS:

(A) LENGTH: 71 base pairs
(B) TYPE: nucleic acid
(C) STRANDEDNESS: single
(D) TOPOLOGY: linear (ix) FEATURE:
(D) OTHER INFORMATION: All C's are 2'-NH2 modified (ix) FEATURE:
(D) OTHER INFORMATION: All U's are 2'-NH2 modified (xi) SEQUENCE DESCRIPTION: SEQ ID NO:23:

GGGAGGACGA UGCGGUGGGA ACGCGGAGGG GAACGUCCUC ACAGCAAUCC 50

ACGGCCAGAC GACUCGCCCG A 71

(2) INFORMATION FOR SEQ ID NO:24:

(i) SEQUENCE CHARACTERISTICS:
(A) LENGTH: 71 base pairs
(B) TYPE: nucleic acid
(C) STRANDEDNESS: single
(D) TOPOLOGY: linear (ix) FEATURE:
(D) OTHER INFORMATION: All C's are 2'-NH2 modified (ix) FEATURE:
(D) OTHER INFORMATION: All U's are 2'-NH2 modified (xi) SEQUENCE DESCRIPTION: SEQ ID NO:24:

GGGAGGACGA UGCGGAGGGU ACGCGGAGGG GUGUGUCCCC CAGACUACAA 50

GGCGGCAGAC GACUCGCCCG A 71

(2) INFORMATION FOR SEQ ID NO:25:

(i) SEQUENCE CHARACTERISTICS:
(A) LENGTH: 17 base pairs
(B) TYPE: nucleic acid
(C) STRANDEDNESS: single
(D) TOPOLOGY: linear (ix) FEATURE:
(B) LOCATION: 1, 5, 17
(D) OTHER INFORMATION: N is U/A (ix) FEATURE:
(D) OTHER INFORMATION: All C's are 2'-NH2 modified (ix) FEATURE:
(D) OTHER INFORMATION: All U's are 2'-NH2 modified (xi) SEQUENCE DESCRIPTION: SEQ ID NO:25:

NGGGNACGCG GAGGGGN 17

(2) INFORMATION FOR SEQ ID NO:26:

(i) SEQUENCE CHARACTERISTICS:
(A) LENGTH: 71 base pairs
(B) TYPE: nucleic acid
(C) STRANDEDNESS: single
(D) TOPOLOGY: linear (ix) FEATURE:
(D) OTHER INFORMATION: All C's are 2'-NH2 modified (ix) FEATURE:
(D) OTHER INFORMATION: All U's are 2'-NH2 modified (xi) SEQUENCE DESCRIPTION: SEQ ID NO:26:

GGGAGGACGA UGCGGCAUAG AAAUAGGAGG AGGAGGAAGG CUAGCCCGCA 50

CGCCCCAGAC GACUCGCCCG A                                                        71

( 2 ) INFORMATION FOR SEQ ID NO:27:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:27:

GGGAGGACGA UGCGGAAAGG AGGAGGCUGG GUGCGUCAAG AGUUCUCCCG                          50

AGCGCCAGAC GACUCGCCCG A                                                        71

( 2 ) INFORMATION FOR SEQ ID NO:28:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:28:

GGGAGGACGA UGCGGUCAGA CGAGGAUGGU GGUAGCGGAG GUAGUGGCUG                          50

AGGGGCAGAC GACUCGCCCG A                                                        71

( 2 ) INFORMATION FOR SEQ ID NO:29:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:29:

GGGAGGACGA UGCGGGUAGA CGCGGGAGGA GGGUGGACGC AGCGGACCGA                          50

ACCCAGACGA CUCGCCCGA                                                           69

( 2 ) INFORMATION FOR SEQ ID NO:30:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:30:

GGGAGGACGA UGCGGAAAGG AGGAGGCUGG GUGAGUCAAG AGUUCUCCCG     50

AGCGCCAGAC GACUCGCCCG A     71

( 2 ) INFORMATION FOR SEQ ID NO:31:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:31:

GGGAGGACGA UGCGG     15

( 2 ) INFORMATION FOR SEQ ID NO:32:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:32:

CAGACGACUC GCCCGA     16

( 2 ) INFORMATION FOR SEQ ID NO:33:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:33:

GGGAGGACGA UGCGGNNNNN NNNNNNNNNN NNNNNNNNNN NNNNNNNNNN     50

NNNNNCAGAC GACUCGCCCG A     71

( 2 ) INFORMATION FOR SEQ ID NO:34:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:34:

GGAGGACGAU GCGGAAAGGA GGAGGCUGGG UGCGUC    36

( 2 ) INFORMATION FOR SEQ ID NO:35:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:35:

GGAGGACGAU GCGGAGGGAA CGCGGAGGGG UG    32

( 2 ) INFORMATION FOR SEQ ID NO:36:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:36:

GGAGGACGAU GCGGUACUGU AAAACAAUCU GGAGGAGGGU CUAGGGGAUG    50

GUGG    54

( 2 ) INFORMATION FOR SEQ ID NO:37:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:37:

GGAGGACGAU GCGGAGGGAA CGCGGAGGGG UGUGUCCCCC AGACUACAAG    50

GCGG    54

( 2 ) INFORMATION FOR SEQ ID NO:38:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:38:

GGAGGACGAU GCGGAAAGGA GGAGGCUGGG UGCGUCAAGA GUUCUCCCGA 50

GCGC 54

( 2 ) INFORMATION FOR SEQ ID NO:39:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:39:

UUGAACGAUC CUU 13

( 2 ) INFORMATION FOR SEQ ID NO:40:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:40:

GGGAGGACGA UGCGGNNNNN NNNNNNNNUU GAACGAUCCU UNNNNNNNN 50

NNNNCAGACG ACUCGCCCGA 70

( 2 ) INFORMATION FOR SEQ ID NO:41:

( i ) SEQUENCE CHARACTERISTICS:
        ( A ) LENGTH: 106 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:41:

GGGAGACAAG AAUAAACGCU CAACAGUGAU UGAACGAUCC UUUCAGCUGG 50

UGGGUAUGGU CCCGGAGUCU CGUUGGUCGU UGAACGAUCC UUCGACAGGA 100

GGCUCA 106

( 2 ) INFORMATION FOR SEQ ID NO:42:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
      ( D ) OTHER INFORMATION: All U's are 2'-NH2 modified ( x i ) SEQUENCE DESCRIPTION: SEQ ID NO:42:

GGGAGGACGA UGCGGCGUGG GGGGGUCUGU CCUUUUCACU AGAAGUGACU     50

CUUCCAGACG ACUCGCCCGA     70

( 2 ) INFORMATION FOR SEQ ID NO:43:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:43:

GGGAGGACGA UGCGGAUGUU GGCAGCAGGG UCCGACGGCG UAACCUUGCC     50

AGCUGCAGAC GACUCGCCCG A     71

( 2 ) INFORMATION FOR SEQ ID NO:44:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:44:

GGGAGGACGA UGCGGAUGUU GGCAGCAGGG UCCGACGGCG UAACCUUGCC     50

GACUGCAGAC GACUCGCCCG A     71

( 2 ) INFORMATION FOR SEQ ID NO:45:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:45:

GGGAGGACGA UGCGGGUACG UAUGGCACAA UUAGGAGGAG GCUGUGGGGU     50

GAUGGCAGAC GACUCGCCCG A     71

( 2 ) INFORMATION FOR SEQ ID NO:46:

( i ) SEQUENCE CHARACTERISTICS:
        ( A ) LENGTH: 71 base pairs
        ( B ) TYPE: nucleic acid
        ( C ) STRANDEDNESS: single (D) TOPOLOGY: linear (ix) FEATURE:
(D) OTHER INFORMATION: All C's are 2'-NH2 modified (ix) FEATURE:
(D) OTHER INFORMATION: All U's are 2'-NH2 modified (xi) SEQUENCE DESCRIPTION: SEQ ID NO:46:

GGGAGGACGA UGCGGGUGGC UUCAGAGGGA GGAACGGAAG AGGCAAAACC 50

ACAGCCAGAC GACUCGCCCG A 71

(2) INFORMATION FOR SEQ ID NO:47:

(i) SEQUENCE CHARACTERISTICS:
(A) LENGTH: 71 base pairs
(B) TYPE: nucleic acid
(C) STRANDEDNESS: single
(D) TOPOLOGY: linear (ix) FEATURE:
(D) OTHER INFORMATION: All C's are 2'-NH2 modified (ix) FEATURE:
(D) OTHER INFORMATION: All U's are 2'-NH2 modified (xi) SEQUENCE DESCRIPTION: SEQ ID NO:47:

GGGAGGACGA UGCGGGUGGC CUCAGAGGGA GGAACGAGAG CAGCUCAGCC 50

AGGGCCAGAC GACUCGCCCG A 71

(2) INFORMATION FOR SEQ ID NO:48:

(i) SEQUENCE CHARACTERISTICS:
(A) LENGTH: 70 base pairs
(B) TYPE: nucleic acid
(C) STRANDEDNESS: single
(D) TOPOLOGY: linear (ix) FEATURE:
(D) OTHER INFORMATION: All C's are 2'-NH2 modified (ix) FEATURE:
(D) OTHER INFORMATION: All U's are 2'-NH2 modified (xi) SEQUENCE DESCRIPTION: SEQ ID NO:48:

GGGAGGACGA UGCGGGUGGC UUCAGAGGGU GGAACGAGAG CAGCUCAGUC 50

AGCCCAGACG ACUCGCCCGA 70

(2) INFORMATION FOR SEQ ID NO:49:

(i) SEQUENCE CHARACTERISTICS:
(A) LENGTH: 70 base pairs
(B) TYPE: nucleic acid
(C) STRANDEDNESS: single
(D) TOPOLOGY: linear (ix) FEATURE:
(D) OTHER INFORMATION: All C's are 2'-NH2 modified (ix) FEATURE:
(D) OTHER INFORMATION: All U's are 2'-NH2 modified (xi) SEQUENCE DESCRIPTION: SEQ ID NO:49:

GGGAGGACGA UGCGGGUGGC UUCAGAGGGU GGAACGAGAG CAGCUCAGCC 50

AGCCCAGACG ACUCGCCCGA 70

(2) INFORMATION FOR SEQ ID NO:50:

( i ) SEQUENCE CHARACTERISTICS:
    ( A ) LENGTH: 71 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-NH2 modified ( i x ) FEATURE:
    ( D ) OTHER INFORMATION: All U's are 2'-NH2 modified ( x i ) SEQUENCE DESCRIPTION: SEQ ID NO:50:

GGGAGGACGA UGCGGGAGGU CAGUGGGUGG AAACGAAGCU GCAGGACUCG         50

CGCUGCAGAC GACUCGCCCG A                                        71

( 2 ) INFORMATION FOR SEQ ID NO:51:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:51:

GGGAGGACGA UGCGGCCAUG AGGCGAGUGG GAGGGAGGUU GAAGCGCACG         50

AUUGGCAGAC GACUCGCCCG A                                        71

( 2 ) INFORMATION FOR SEQ ID NO:52:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:52:

GGGAGGACGA UGCGGGAGGU CAGAGGGUGG CACCGAAAAG AAAGGAGUUC         50

GCCCCCAGAC GACUCGCCCG A                                        71

( 2 ) INFORMATION FOR SEQ ID NO:53:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:53:

GGGAGGACGA UGCGGUUUGA GGAGAGCGGG UGGGUGGAAC GCAGGAGUAG         50

UCAGCAGACG ACUCGCCCGA                                          70

( 2 ) INFORMATION FOR SEQ ID NO:54:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:54:

GGGAGGACGA UGCGGCACGU AGAGCUAGUG GAGGGUAGUA GUACACAACU 50

AAAUACAGAC GACUCGCCCG A 71

( 2 ) INFORMATION FOR SEQ ID NO:55:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:55:

GGGAGGACGA UGCGGUUUGA GGAGAGCGGG UGGGUGGAAC GCAGGAGUAG 50

UCCGCCAGAC GACUCGCCCG A 71

( 2 ) INFORMATION FOR SEQ ID NO:56:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:56:

GGGAGGACGA UGCGGGUACG UAUGGCACAA UUAGGAGGAG GCUCUGGGGU 50

GUUGGCAGAC GACUCGCCCG A 71

( 2 ) INFORMATION FOR SEQ ID NO:57:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:57:

GGGAGGACGA UGCGGAGGCU GGAGGGUGGA GGGAUGCAUG CAGUAUACCG        50

CACCGCAGAC GACUCGCCCG A        71

( 2 ) INFORMATION FOR SEQ ID NO:58:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:58:

GGGAGGACGA UGCGGAAUCA CAUGUGGUGG GUACGUGGAG GGGAAAUUGC        50

CGCCCAGACG ACUCGCCCGA        70

( 2 ) INFORMATION FOR SEQ ID NO:59:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:59:

GGGAGGACGA UGCGGCACGA GGCUAGUGGA GGGUAGCAGU GGAGGGUACU        50

GCCAGACGAC UCGCCCGA        68

( 2 ) INFORMATION FOR SEQ ID NO:60:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
        ( D ) OTHER INFORMATION: All U's are 2'-NH2 modified ( x i ) SEQUENCE DESCRIPTION: SEQ ID NO:60:

GGGAGGACGA UGCGGCACGA GGCUAGUGGA GGGUAGCAGU GGAGGGGUAC        50

GCUGCCAGAC GACUCGCCCG A        71

( 2 ) INFORMATION FOR SEQ ID NO:61:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH2 modified ( i x ) FEATURE:
    ( D ) OTHER INFORMATION: All U's are 2'-NH2 modified ( x i ) SEQUENCE DESCRIPTION: SEQ ID NO:61:

GGGAGGACGA UGCGGAAUCA CAUGUGGAGG GUACGUGGAG GGGAAAUGGU  50

GACCGCAGAC GACUCGCCCG A  71

( 2 ) INFORMATION FOR SEQ ID NO:62:

( i ) SEQUENCE CHARACTERISTICS:
　　　　( A ) LENGTH: 69 base pairs
　　　　( B ) TYPE: nucleic acid
　　　　( C ) STRANDEDNESS: single
　　　　( D ) TOPOLOGY: linear ( i x ) FEATURE:
　　　　( D ) OTHER INFORMATION: All C's are 2'-NH2 modified ( i x ) FEATURE:
　　　　( D ) OTHER INFORMATION: All U's are 2'-NH2 modified ( x i ) SEQUENCE DESCRIPTION: SEQ ID NO:62:

GGGAGGACGA UGCGGCACGA GGCUAGUGGA GGGUAGCAGU GGAGGGGUAG  50

UGCCAGACGA CUCGCCCGA  69

( 2 ) INFORMATION FOR SEQ ID NO:63:

( i ) SEQUENCE CHARACTERISTICS:
　　　　( A ) LENGTH: 68 base pairs
　　　　( B ) TYPE: nucleic acid
　　　　( C ) STRANDEDNESS: single
　　　　( D ) TOPOLOGY: linear ( i x ) FEATURE:
　　　　( D ) OTHER INFORMATION: All C's are 2'-NH2 modified ( i x ) FEATURE:
　　　　( D ) OTHER INFORMATION: All U's are 2'-NH2 modified ( x i ) SEQUENCE DESCRIPTION: SEQ ID NO:63:

GGGAGGACGA UGCGGAAUCA CAUGUGGUGG GUACGUGGAG GGGAAUGCGA  50

CCCAGACGAC UCGCCCGA  68

( 2 ) INFORMATION FOR SEQ ID NO:64:

( i ) SEQUENCE CHARACTERISTICS:
　　　　( A ) LENGTH: 87 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:64:

GGGAGACAAG AATAAACGCT CAANNNNNN NNNNNNNNN NNNNNNNNN  50

NNNNNNNNN NNNTTCGACA GGAGGCTCAC AACAGGC  87

( 2 ) INFORMATION FOR SEQ ID NO:65:

( i ) SEQUENCE CHARACTERISTICS:
　　　　( A ) LENGTH: 40 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:65:

TAATACGACT CACTATAGGG AGACAAGAAT AAACGCTCAA  40

( 2 ) INFORMATION FOR SEQ ID NO:66:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

| | |
|---|---:|
| GCCTGTTGTG AGCCTCCTGT CGAA | 24 |

( 2 ) INFORMATION FOR SEQ ID NO:67:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

| | |
|---|---:|
| CAGAAGCTTA ATACGACTCA CTATAGGGAG ACAAGAATAA ACGCTCAA | 48 |

( 2 ) INFORMATION FOR SEQ ID NO:68:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

| | |
|---|---:|
| GACTGGATCC GCCTGTTGTG AGCCTCCTGT CGAA | 34 |

( 2 ) INFORMATION FOR SEQ ID NO:69:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:69:

| | |
|---|---:|
| TAATACGACT CACTATAGGG AGTCTCGTTG GTCGTTGAAC GATCCTTCGA | 50 |
| CAGGAGGCTC A | 61 |

( 2 ) INFORMATION FOR SEQ ID NO:70:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:70:

| | |
|---|---:|
| TAATACGACT CACTATAG | 18 |

( 2 ) INFORMATION FOR SEQ ID NO:71:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

| | |
|---|---:|
| TGAGCCTCCT GTCGAAGGAT C | 21 |

( 2 ) INFORMATION FOR SEQ ID NO:72:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:72:

```
GGGAGACAAG  AATAAACGCT  CAACAGTGAT  TGAACGATCC  TTTCAGCTGG            50

TGGGTA                                                                56
```

( 2 ) INFORMATION FOR SEQ ID NO:73:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:73:

```
TGGTCCCGGA  GTCTCGTTGG  TCGTTGAACG  ATCCTTCGAC  AGGAGGCTCA            50
```

( 2 ) INFORMATION FOR SEQ ID NO:74:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:74:

```
CCGGGACCAT  ACCCACCA                                                  18
```

( 2 ) INFORMATION FOR SEQ ID NO:75:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:75:

```
TGAGCCTCCT  GTCGAAGG                                                  18
```

( 2 ) INFORMATION FOR SEQ ID NO:76:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:76:

```
GGGAGGACGA  TGCGGNNNNN  NNNNNNNTT   GAACGATCCT  TNNNNNNNN             50

NNNNCAGACG  ACTCGCCCGA                                                70
```

( 2 ) INFORMATION FOR SEQ ID NO:77:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:77:

```
TAATACGACT  CACTATAGGG  AGGACGATGC  GG                                32
```

( 2 ) INFORMATION FOR SEQ ID NO:78:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:78:

| | |
|---|---|
| TCGGGCGAGT CGTCTG | 16 |

( 2 ) INFORMATION FOR SEQ ID NO:79:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:79:

| | |
|---|---|
| GGGAGACAAG AAUAAACGCU CAANNNNNNN NNNNNNNNN NNNNNNNNN | 50 |
| NNNNNNNNN NNNUUCGACA GGAGGCUCAC AACAGGC | 87 |

( 2 ) INFORMATION FOR SEQ ID NO:80:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:80:

| | |
|---|---|
| GGGAGACAAG AAUAAACGCU CAAUUGGAA GAUCCCGGAG UCUCGUUGGU | 50 |
| CGUUGAACGA UCCUUCGACA GGAGGCUCAC AACAGGG | 87 |

( 2 ) INFORMATION FOR SEQ ID NO:81:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:81:

| | |
|---|---|
| GGGAGACAAG AAUAAACGCU CAAUUGGAA GAUCCCGGAG UCUCGUUGGU | 50 |
| GUUGAACGAU UCUUCGACAG GAGGCUCACA ACAGGC | 86 |

( 2 ) INFORMATION FOR SEQ ID NO:82:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F modified ( i x ) FEATURE:
    ( D ) OTHER INFORMATION: All U's are 2'-F modified ( x i ) SEQUENCE DESCRIPTION: SEQ ID NO:82:

```
GGGAGACAAG AAUAAACGCU CAAUUUAGAA GAUCCCGGAG UCUCGUUGGU        50
CGUUGAACGA UCCUUCGACA GGAGGCUCAC AACAGGC                      87
```

( 2 ) INFORMATION FOR SEQ ID NO:83:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F modified ( i x ) FEATURE:
    ( D ) OTHER INFORMATION: All U's are 2'-F modified ( x i ) SEQUENCE DESCRIPTION: SEQ ID NO:83:

```
GGGAGACAAG AAUAAACGCU CAAUUCGGAA GAUCACGGAG UCUCGUUGGU        50
CGUUGAACGA UCCUUCGACA GGAGGCUCAC AACAGGC                      87
```

( 2 ) INFORMATION FOR SEQ ID NO:84:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F modified ( i x ) FEATURE:
    ( D ) OTHER INFORMATION: All U's are 2'-F modified ( x i ) SEQUENCE DESCRIPTION: SEQ ID NO:84:

```
GGGAGACAAG AAUAAACGCU CAAUUUGGAA GAUCCCGAGA UCUCGUUGGU        50
CGUUGAACGA UCCUUCGACA GGAGGCUCAC AACAGGC                      87
```

( 2 ) INFORMATION FOR SEQ ID NO:85:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F modified ( i x ) FEATURE:
    ( D ) OTHER INFORMATION: All U's are 2'-F modified ( x i ) SEQUENCE DESCRIPTION: SEQ ID NO:85:

```
GGGAGACAAG AAUAAACGCU CAAUUUGGAA GAUCCCAGAG UCUCGUUGGU        50
CGUUGAACGA UCCUUCGACA GGAGGCUCAC AACAGGC                      87
```

( 2 ) INFORMATION FOR SEQ ID NO:86:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F modified ( i x ) FEATURE:
    ( D ) OTHER INFORMATION: All U's are 2'-F modified ( x i ) SEQUENCE DESCRIPTION: SEQ ID NO:86:

GGGAGACAAG AAUAAACGCU CAAUUCGGAA GAUCCCAGAG UCUCGUUGGU   50

CGUUGAACGA UCCUUCGACA GGAGGCUCAC AACAGGC   87

( 2 ) INFORMATION FOR SEQ ID NO:87:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F modified ( i x ) FEATURE:
    ( D ) OTHER INFORMATION: All U's are 2'-F modified ( x i ) SEQUENCE DESCRIPTION: SEQ ID NO:87:

GGGAGACAAG AAUAAACGCU CAAUUCUGAA GAUCCCAGAG UCUCGUUGGU   50

CGUUGAACGA UCCUUCGACA GGAGGCUCAC AACAGGC   87

( 2 ) INFORMATION FOR SEQ ID NO:88:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F modified ( i x ) FEATURE:
    ( D ) OTHER INFORMATION: All U's are 2'-F modified ( x i ) SEQUENCE DESCRIPTION: SEQ ID NO:88:

GGGAGACAAG AAUAAACGCU CAAUUUGGAA GAUCCCAGAG UCUCGUUGGU   50

CGUUAAACGA UCCUUCGACA GGAGGCUCAC AACAGGC   87

( 2 ) INFORMATION FOR SEQ ID NO:89:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F modified ( i x ) FEATURE:
    ( D ) OTHER INFORMATION: All U's are 2'-F modified ( x i ) SEQUENCE DESCRIPTION: SEQ ID NO:89:

GGGAGACAAG AAUAAACGCU CAAUUUGGAA GAUCCCUGAG UCUCGUUGGU                    50

CGUUGAACGA UCCUUCGACA GGAGGCUCAC AACAGGC                                 87

( 2 ) INFORMATION FOR SEQ ID NO:90:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:90:

GGGAGACAAG AAUAAACGCU CAAUUUCGAA GAUCCCUGAG UCUCGUUGGU                    50

CGUUGAACGA UCCUUCGACA GGAGGCUCAC AACAGGC                                 87

( 2 ) INFORMATION FOR SEQ ID NO:91:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:91:

GGGAGACAAG AAUAAACGCU CAAUUGGAA GAUCCCUGGA GUCUCGUUGG                     50

UCGUUGAACG AUCCUUCGAC AGGAGGCUCA CAACAGGC                                 88

( 2 ) INFORMATION FOR SEQ ID NO:92:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:92:

GGGAGACAAG AAUAAACGCU CAAUUUGGAA GGUCCUGAGU CUCGUUGGUC                    50

GUUGAACGAU CCUUCGACAG GAGGCUCACA ACAGGC                                  86

( 2 ) INFORMATION FOR SEQ ID NO:93:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
  ( D ) OTHER INFORMATION: All U's are 2'-F modified ( x i ) SEQUENCE DESCRIPTION: SEQ ID NO:93:

GGGAGACAAG AAUAAACGCU CAAAUUGGAG UAUCCCUGAG UCUUGUUGGU        50

CGUUGAACGG UCCUUCGACA GGAGGCUCAC AACAGGC        87

( 2 ) INFORMATION FOR SEQ ID NO:94:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F modified ( i x ) FEATURE:
    ( D ) OTHER INFORMATION: All U's are 2'-F modified ( x i ) SEQUENCE DESCRIPTION: SEQ ID NO:94:

GGGAGACAAG AAUAAACGCU CAAAGUCCC UCGCAGAGCU UGCUGGUUCG        50

AUUGAACGAU CCUUUCGACA GGAGGCUCAC AACAGGC        87

( 2 ) INFORMATION FOR SEQ ID NO:95:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F modified ( i x ) FEATURE:
    ( D ) OTHER INFORMATION: All U's are 2'-F modified ( x i ) SEQUENCE DESCRIPTION: SEQ ID NO:95:

GGGAGACAAG AAUAAACGCU CAAAGUCAC UCGCAGCGCU UCCUGGUUCG        50

AUUGAACGAU CCUUUCGACA GGAGGCUCAC AACAGGC        87

( 2 ) INFORMATION FOR SEQ ID NO:96:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F modified ( i x ) FEATURE:
    ( D ) OTHER INFORMATION: All U's are 2'-F modified ( x i ) SEQUENCE DESCRIPTION: SEQ ID NO:96:

GGGAGACAAG AAUAAACGCU CAAAGCCCC UCGCAUAGCU UCCUCGUUCG        50

AUUGAACGAU CCCUUCGACA GGAGGCUCAC AACAGGC        87

( 2 ) INFORMATION FOR SEQ ID NO:97:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: linear ( i x ) FEATURE:
   ( D ) OTHER INFORMATION: All C's are 2'-F modified ( i x ) FEATURE:
   ( D ) OTHER INFORMATION: All U's are 2'-F modified ( x i ) SEQUENCE DESCRIPTION: SEQ ID NO:97:

GGGAGACAAG AAUAAACGCU CAAGUGCCCU GUUAUCUUCC UCGAUCGAUU     50

GAACGAUCCU UUCGACAGGA GGCUCACAAC AGGC     84

( 2 ) INFORMATION FOR SEQ ID NO:98:

( i ) SEQUENCE CHARACTERISTICS:
      ( A ) LENGTH: 87 base pairs
      ( B ) TYPE: nucleic acid
      ( C ) STRANDEDNESS: single
      ( D ) TOPOLOGY: linear ( i x ) FEATURE:
      ( D ) OTHER INFORMATION: All C's are 2'-F modified ( i x ) FEATURE:
      ( D ) OTHER INFORMATION: All U's are 2'-F modified ( x i ) SEQUENCE DESCRIPTION: SEQ ID NO:98:

GGGAGACAAG AAUAAACGCU CAACCAGAUA AUCCCAAUGA GUCCCUCGAG     50

AUUGAACGAU CCUUUCGACA GGAGGCUCAC AACAGGC     87

( 2 ) INFORMATION FOR SEQ ID NO:99:

( i ) SEQUENCE CHARACTERISTICS:
      ( A ) LENGTH: 85 base pairs
      ( B ) TYPE: nucleic acid
      ( C ) STRANDEDNESS: single
      ( D ) TOPOLOGY: linear ( i x ) FEATURE:
      ( D ) OTHER INFORMATION: All C's are 2'-F modified ( i x ) FEATURE:
      ( D ) OTHER INFORMATION: All U's are 2'-F modified ( x i ) SEQUENCE DESCRIPTION: SEQ ID NO:99:

GGGAGACAAG AAUAAACGCU CAAGUCAUAA GCCUAACGGU CCCUAGUCAA     50

UUGAACGAUC CUUCGACAGG AGGCUCACAA CAGGC     85

( 2 ) INFORMATION FOR SEQ ID NO:100:

( i ) SEQUENCE CHARACTERISTICS:
      ( A ) LENGTH: 85 base pairs
      ( B ) TYPE: nucleic acid
      ( C ) STRANDEDNESS: single
      ( D ) TOPOLOGY: linear ( i x ) FEATURE:
      ( D ) OTHER INFORMATION: All C's are 2'-F modified ( i x ) FEATURE:
      ( D ) OTHER INFORMATION: All U's are 2'-F modified ( x i ) SEQUENCE DESCRIPTION: SEQ ID NO:100:

GGGAGACAAG AAUAAACGCU CAACAGCGAU UGAACGAUCC UUUCAGCUGA     50

UGGGUAUGGG AUUCGACAGG AGGCUCACAA CAGGC     85

( 2 ) INFORMATION FOR SEQ ID NO:101:

( i ) SEQUENCE CHARACTERISTICS:

(A) LENGTH: 86 base pairs
(B) TYPE: nucleic acid
(C) STRANDEDNESS: single
(D) TOPOLOGY: linear (ix) FEATURE:
(D) OTHER INFORMATION: All C's are 2'-F modified (ix) FEATURE:
(D) OTHER INFORMATION: All U's are 2'-F modified (xi) SEQUENCE DESCRIPTION: SEQ ID NO:101:

GGGAGACAAG AAUAAACGCU CAAACAGCGA UUGAACGAUC CUUUCAGCUG           50

AUGGGUACGG GAUUCGACAG GAGGCUCACA ACAGGC                          86

(2) INFORMATION FOR SEQ ID NO:102:

(i) SEQUENCE CHARACTERISTICS:
(A) LENGTH: 85 base pairs
(B) TYPE: nucleic acid
(C) STRANDEDNESS: single
(D) TOPOLOGY: linear (ix) FEATURE:
(D) OTHER INFORMATION: All C's are 2'-F modified (ix) FEATURE:
(D) OTHER INFORMATION: All U's are 2'-F modified (xi) SEQUENCE DESCRIPTION: SEQ ID NO:102:

GGGAGACAAG AAUAAACGCU CAACAGUGAU UGAACGAUCC UUUCAGCUGG           50

UGGGUAUGGG GUUCGACAGG AGGCUCACAA CAGGC                           85

(2) INFORMATION FOR SEQ ID NO:103:

(i) SEQUENCE CHARACTERISTICS:
(A) LENGTH: 84 base pairs
(B) TYPE: nucleic acid
(C) STRANDEDNESS: single
(D) TOPOLOGY: linear (ix) FEATURE:
(D) OTHER INFORMATION: All C's are 2'-F modified (ix) FEATURE:
(D) OTHER INFORMATION: All U's are 2'-F modified (xi) SEQUENCE DESCRIPTION: SEQ ID NO:103:

GGGAGACAAG AAUAAACGCU CAACAGUGAU UGAACGAUCC UUCAGCUGAU           50

GGGUAUGGGA UUCGACAGGA GGCUCACAAC AGGC                            84

(2) INFORMATION FOR SEQ ID NO:104:

(i) SEQUENCE CHARACTERISTICS:
(A) LENGTH: 83 base pairs
(B) TYPE: nucleic acid
(C) STRANDEDNESS: single
(D) TOPOLOGY: linear (ix) FEATURE:
(D) OTHER INFORMATION: All C's are 2'-F modified (ix) FEATURE:
(D) OTHER INFORMATION: All U's are 2'-F modified (xi) SEQUENCE DESCRIPTION: SEQ ID NO:104:

GGGAGACAAG AAUAAACGCU CAACAGCGAU UGAACGACCU UCAGCUGAUG           50

GGUAUGGGAU UCGACAGGAG GCUCACAACA GGC                             83

( 2 ) INFORMATION FOR SEQ ID NO:105:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:105:

```
GGGAGACAAG  AAUAAACGCU  CAACCAAAGG  AGCAUCUGUC  GUUAUGGGAG        50
GACGAGGAAG  GGUUCGACAG  GAGGCUCACA  ACAGGC                        86
```

( 2 ) INFORMATION FOR SEQ ID NO:106:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:106:

```
GGGAGACAAG  AAUAAACGCU  CAACCAAAGG  AGCAUCUGUC  GUUAUGGGAG        50
GAUGAGGGAA  GGGUUCGACA  GGAGGCUCAC  AACAGGC                       87
```

( 2 ) INFORMATION FOR SEQ ID NO:107:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:107:

```
GGGAGACAAG  AAUAAACGCU  CAACCAAAGG  AGCAUCUGUU  GUUAUGGGAG        50
GAUGAGGGAA  GGGUUCGACA  GGAGGCUCAC  AACAGGC                       87
```

( 2 ) INFORMATION FOR SEQ ID NO:108:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:108:

GGGAGACAAG AAUAAACGCU CAACCAAUUG AGAACCGUCG AUGUGGGAGG 50

GAGGGAGGAA UUCGACAGGA GGCUCACAAC AGGC 84

( 2 ) INFORMATION FOR SEQ ID NO:109:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:109:

GGGAGACAAG AAUAAACGCU CAAUGAGUCA ACAAAGAAAU GGAGGGAGGA 50

GAGGGAGGAA UUUCGACAGG AGGCUCACAA CAGGC 85

( 2 ) INFORMATION FOR SEQ ID NO:110:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:110:

GGGAGACAAG AAUAAACGCU CAAUGAGCAA CCAGAGAAUG GAGGAGGAGA 50

GGGAGGAAUU UCGACAGGAG GCUCACAACA GGC 83

( 2 ) INFORMATION FOR SEQ ID NO:111:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:111:

GGGAGACAAG AAUAAACGCU CAAUGAGCCA ACCAAAGGAA UGGAGGGAGG 50

AGAGGGAGGA GUUUCGACAG GAGGCUCACA ACAGGC 86

( 2 ) INFORMATION FOR SEQ ID NO:112:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:

( D ) OTHER INFORMATION: All U's are 2'-F modified ( x i ) SEQUENCE DESCRIPTION: SEQ ID NO:112:

GGGAGACAAG AAUAAACGCU CAAUGAUGGG CUACUCGGGA UCGAAAGAGG 50

GUGGGAGGGA GGAUUCGACA GGAGGCUCAC AACAGGC 87

( 2 ) INFORMATION FOR SEQ ID NO:113:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:113:

GGGAGACAAG AAUAAACGCU CAAUGUGAGG GUGGAAUAGG AGGGAGGUAU 50

UUGAGCUGGA ACUUCGACAG GAGGCUCACA ACAGGC 86

( 2 ) INFORMATION FOR SEQ ID NO:114:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:114:

GGGAGACAAG AAUAAACGCU CAAGUGGUAG AUAUGAGGGA AGGGUGGGAG 50

GCAACACUAG GAUUCGACAG GAGGCUCACA ACAGGC 86

( 2 ) INFORMATION FOR SEQ ID NO:115:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:115:

GGGAGACAAG AAUAAACGCU CAAGAUCGAA GACAACGUGG GUGGGAGGGA 50

GGUAAAUGUA CCUUCGACAG GAGGCUCACA ACAGGC 86

( 2 ) INFORMATION FOR SEQ ID NO:116:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i x ) FEATURE:
  ( D ) OTHER INFORMATION: All C's are 2'-F modified ( i x ) FEATURE:
  ( D ) OTHER INFORMATION: All U's are 2'-F modified ( x i ) SEQUENCE DESCRIPTION: SEQ ID NO:116:

GGGAGACAAG AAUAAACGCU CAACAGUGGA GGGAGGUUAU GAGGGUGGAU 50

GUUAAAGCGC AAUUCGACAG GAGGCUCACA ACAGGC 86

( 2 ) INFORMATION FOR SEQ ID NO:117:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F modified ( i x ) FEATURE:
    ( D ) OTHER INFORMATION: All U's are 2'-F modified ( x i ) SEQUENCE DESCRIPTION: SEQ ID NO:117:

GGGAGUCUCG UUGGUCGUUG AACGAUCCUU CGACAGGAGG CUCA 44

( 2 ) INFORMATION FOR SEQ ID NO:118:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F modified ( i x ) FEATURE:
    ( D ) OTHER INFORMATION: All U's are 2'-F modified ( x i ) SEQUENCE DESCRIPTION: SEQ ID NO:118:

GGGAGGACGA UGCGGGUUCG ACAUAAUCUU GAACGAUCCU UGAUUACUUG 50

GUCCCAGACG ACUCGCCCGA 70

( 2 ) INFORMATION FOR SEQ ID NO:119:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-F modified ( i x ) FEATURE:
    ( D ) OTHER INFORMATION: All U's are 2'-F modified ( x i ) SEQUENCE DESCRIPTION: SEQ ID NO:119:

GGGAGGACGA UGCGGCAUUC GCUGAUUCUU GAACGAUCCU UGAUGAUGUG 50

GAUGCAGACG ACUCGCCCGA 70

( 2 ) INFORMATION FOR SEQ ID NO:120:

( i ) SEQUENCE CHARACTERISTICS:
    ( A ) LENGTH: 70 base pairs
    ( B ) TYPE: nucleic acid
    ( C ) STRANDEDNESS: single ( D ) TOPOLOGY: linear ( i x ) FEATURE:
( D ) OTHER INFORMATION: All C's are 2'-F modified ( i x ) FEATURE:
( D ) OTHER INFORMATION: All U's are 2'-F modified ( x i ) SEQUENCE DESCRIPTION: SEQ ID NO:120:

GGGAGGACGA UGCGGUUCUA CACGAUAUUU GAACGAUCCU UGUAUCUUAG    50

GUCCCAGACG ACUCGCCCGA    70

( 2 ) INFORMATION FOR SEQ ID NO:121:

( i ) SEQUENCE CHARACTERISTICS:
( A ) LENGTH: 70 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F modified ( i x ) FEATURE:
( D ) OTHER INFORMATION: All U's are 2'-F modified ( x i ) SEQUENCE DESCRIPTION: SEQ ID NO:121:

GGGAGGACGA UGCGGUAACU CUUAAUUCUU GAACAAUCCU UGAAUUUAGC    50

GGACCAGACG ACUCGCCCGA    70

( 2 ) INFORMATION FOR SEQ ID NO:122:

( i ) SEQUENCE CHARACTERISTICS:
( A ) LENGTH: 69 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F modified ( i x ) FEATURE:
( D ) OTHER INFORMATION: All U's are 2'-F modified ( x i ) SEQUENCE DESCRIPTION: SEQ ID NO:122:

GGGAGGACGA UGCGGAUUCG AUGUAGUUUG AACGAUCCUU GUAUAUACG    50

GAUCAGACGA CUCGCCCGA    69

( 2 ) INFORMATION FOR SEQ ID NO:123:

( i ) SEQUENCE CHARACTERISTICS:
( A ) LENGTH: 69 base pairs
( B ) TYPE: nucleic acid
( C ) STRANDEDNESS: single
( D ) TOPOLOGY: linear ( i x ) FEATURE:
( D ) OTHER INFORMATION: All C's are 2'-F modified ( i x ) FEATURE:
( D ) OTHER INFORMATION: All U's are 2'-F modified ( x i ) SEQUENCE DESCRIPTION: SEQ ID NO:123:

GGGAGGACGA UGCGGUUCGA UUCCAAGUUG AACGAUCCUC CUUUUGAUUA    50

GACCAGACGA CUCGCCCGA    69

( 2 ) INFORMATION FOR SEQ ID NO:124:

( i ) SEQUENCE CHARACTERISTICS:
   ( A ) LENGTH: 70 base pairs
   ( B ) TYPE: nucleic acid
   ( C ) STRANDEDNESS: single
   ( D ) TOPOLOGY: linear ( i x ) FEATURE:
   ( D ) OTHER INFORMATION: All C's are 2'-F modified ( i x ) FEATURE:
   ( D ) OTHER INFORMATION: All U's are 2'-F modified ( x i ) SEQUENCE DESCRIPTION: SEQ ID NO:124:

GGGAGGACGA UGCGGUUCGA CACGAAAGUU GAACGAUCCU UCUAUCUGUU           50

GGACCAGACG ACUCGCCCGA                                            70

( 2 ) INFORMATION FOR SEQ ID NO:125:

( i ) SEQUENCE CHARACTERISTICS:
      ( A ) LENGTH: 70 base pairs
      ( B ) TYPE: nucleic acid
      ( C ) STRANDEDNESS: single
      ( D ) TOPOLOGY: linear ( i x ) FEATURE:
      ( D ) OTHER INFORMATION: All C's are 2'-F modified ( i x ) FEATURE:
      ( D ) OTHER INFORMATION: All U's are 2'-F modified ( x i ) SEQUENCE DESCRIPTION: SEQ ID NO:125:

GGGAGGACGA UGCGGGUUUA AUACAAAGUU GAACGAUCCU UCUUUGCAUU           50

GGACCAGACG ACUCGCCCGA                                            70

( 2 ) INFORMATION FOR SEQ ID NO:126:

( i ) SEQUENCE CHARACTERISTICS:
      ( A ) LENGTH: 70 base pairs
      ( B ) TYPE: nucleic acid
      ( C ) STRANDEDNESS: single
      ( D ) TOPOLOGY: linear ( i x ) FEATURE:
      ( D ) OTHER INFORMATION: All C's are 2'-F modified ( i x ) FEATURE:
      ( D ) OTHER INFORMATION: All U's are 2'-F modified ( x i ) SEQUENCE DESCRIPTION: SEQ ID NO:126:

GGGAGGACGA UGCGGGUUUC ACUUCAAGUU GAACGAUCCU UCUUGGCUUG           50

AGCACAGACG ACUCGCCCGA                                            70

( 2 ) INFORMATION FOR SEQ ID NO:127:

( i ) SEQUENCE CHARACTERISTICS:
      ( A ) LENGTH: 70 base pairs
      ( B ) TYPE: nucleic acid
      ( C ) STRANDEDNESS: single
      ( D ) TOPOLOGY: linear ( i x ) FEATURE:
      ( D ) OTHER INFORMATION: All C's are 2'-F modified ( i x ) FEATURE:
      ( D ) OTHER INFORMATION: All U's are 2'-F modified ( x i ) SEQUENCE DESCRIPTION: SEQ ID NO:127:

GGGAGGACGA UGCGGGUUUA AUCUCGGAUU GAACGAUCCU UUCUGUAAUU           50

AGUCCAGACG ACUCGCCCGA                                            70

( 2 ) INFORMATION FOR SEQ ID NO:128:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:128:

| | | | | | |
|---|---|---|---|---|---|
| GGGAGGACGA | UGCGGAUGAG | CUUGAUAAUG | GAACGAUCCU | UUUAACGGUU | 5 0 |
| CUUCCAGACG | ACUCGCCCGA | | | | 7 0 |

( 2 ) INFORMATION FOR SEQ ID NO:129:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:129:

| | | | | | |
|---|---|---|---|---|---|
| GGGAGGACGA | UGCGGAACAC | CAAUCUUUUU | GAACGAUCCU | UCGUGGGAGU | 5 0 |
| GCAUCAGACG | ACUCGCCCGA | | | | 7 0 |

( 2 ) INFORMATION FOR SEQ ID NO:130:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:130:

| | | | | | |
|---|---|---|---|---|---|
| GGGAGGACGA | UGCGGGAUUC | UCUUUGAGUU | GAACGAUCCU | UCUCAUCGCA | 5 0 |
| CUUGCCAGAC | GACUCGCCCG | A | | | 7 1 |

( 2 ) INFORMATION FOR SEQ ID NO:131:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:131:

GGGAGGACGA UGCGGUUUGA CGUAUAAUUG AACGAUCCUU UUCUAGCUUA 50

GACCAGACGA CUCGCCCGA 69

(2) INFORMATION FOR SEQ ID NO:132:

(i) SEQUENCE CHARACTERISTICS:
  (A) LENGTH: 70 base pairs
  (B) TYPE: nucleic acid
  (C) STRANDEDNESS: single
  (D) TOPOLOGY: linear (ix) FEATURE:
  (D) OTHER INFORMATION: All C's are 2'-F modified (ix) FEATURE:
  (D) OTHER INFORMATION: All U's are 2'-F modified (xi) SEQUENCE DESCRIPTION: SEQ ID NO:132:

GGGAGGACGA UGCGGUGUUC AUGCUUGAUU GAACGAUCCU UUCAUAGUGU 50

UGGUCAGACG ACUCGCCCGA 70

(2) INFORMATION FOR SEQ ID NO:133:

(i) SEQUENCE CHARACTERISTICS:
  (A) LENGTH: 70 base pairs
  (B) TYPE: nucleic acid
  (C) STRANDEDNESS: single
  (D) TOPOLOGY: linear (ix) FEATURE:
  (D) OTHER INFORMATION: All C's are 2'-F modified (ix) FEATURE:
  (D) OTHER INFORMATION: All U's are 2'-F modified (xi) SEQUENCE DESCRIPTION: SEQ ID NO:133:

GGGAGGACGA UGCGGUUCCU GAUUCAAGUU GAACGAUCCU UCCUGCUGUA 50

CGUCCAGACG ACUCGCCCGA 70

(2) INFORMATION FOR SEQ ID NO:134:

(i) SEQUENCE CHARACTERISTICS:
  (A) LENGTH: 70 base pairs
  (B) TYPE: nucleic acid
  (C) STRANDEDNESS: single
  (D) TOPOLOGY: linear (ix) FEATURE:
  (D) OTHER INFORMATION: All C's are 2'-F modified (ix) FEATURE:
  (D) OTHER INFORMATION: All U's are 2'-F modified (xi) SEQUENCE DESCRIPTION: SEQ ID NO:134:

GGGAGGACGA UGCGGGUUCG AUUUACCUUU GAACGAUCCU UACUUAGCUU 50

CCACCAGACG ACUCGCCCGA 70

(2) INFORMATION FOR SEQ ID NO:135:

(i) SEQUENCE CHARACTERISTICS:
  (A) LENGTH: 69 base pairs
  (B) TYPE: nucleic acid
  (C) STRANDEDNESS: single
  (D) TOPOLOGY: linear (ix) FEATURE:
  (D) OTHER INFORMATION: All C's are 2'-F modified (ix) FEATURE:
        (D) OTHER INFORMATION: All U's are 2'-F modified (xi) SEQUENCE DESCRIPTION: SEQ ID NO:135:

GGGAGGACGA UGCGGUUCGA UGGCCAUUUG AACGAUCCUU AUUAUCAACG        50

GUCCAGACGA CUCGCCCGA        69

(2) INFORMATION FOR SEQ ID NO:136:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ix) FEATURE:
        (D) OTHER INFORMATION: All C's are 2'-F modified (ix) FEATURE:
        (D) OTHER INFORMATION: All U's are 2'-F modified (xi) SEQUENCE DESCRIPTION: SEQ ID NO:136:

GGGAGGACGA UGCGGAAUUC CCCCAAGAUU GAACGGUCCU UUCUCGCAGA        50

UGUUCAGACG ACUCGCCCGA        70

(2) INFORMATION FOR SEQ ID NO:137:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ix) FEATURE:
        (D) OTHER INFORMATION: All C's are 2'-F modified (ix) FEATURE:
        (D) OTHER INFORMATION: All U's are 2'-F modified (xi) SEQUENCE DESCRIPTION: SEQ ID NO:137:

GGGAGGACGA UGCGGGUUCG AAACUUCCUU GAACGAUCCU UGGAUGUUUU        50

GCUCAGACGA CUCGCCCGA        69

(2) INFORMATION FOR SEQ ID NO:138:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ix) FEATURE:
        (D) OTHER INFORMATION: All C's are 2'-F modified (ix) FEATURE:
        (D) OTHER INFORMATION: All U's are 2'-F modified (xi) SEQUENCE DESCRIPTION: SEQ ID NO:138:

GGGAGGACGA UGCGGUUCGU CAUCGCUAUU GAACGAUCCU UUAGCUGAUG        50

GACCAGACGA CUCGCCCGA        69

(2) INFORMATION FOR SEQ ID NO:139:

(i) SEQUENCE CHARACTERISTICS:
        (A) LENGTH: 68 base pairs
        (B) TYPE: nucleic acid
        (C) STRANDEDNESS: single
        (D) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:139:

GGGAGGACGA UGCGGGAUUU UCCGUUAAUU GAACGAUCCU UUUCACGGAC   50

UGCAGACGAC UCGCCCGA   68

( 2 ) INFORMATION FOR SEQ ID NO:140:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:140:

GGGAGGACGA UGCGGUCUUA AGUUUGAAUU GAACGAUCCU UUUCUUCCAG   50

GCAACAGACG ACUCGCCCGA   70

( 2 ) INFORMATION FOR SEQ ID NO:141:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:141:

GGGAGGACGA UGCGGUUUAG UGUUUAGUUG AACGAUCCUU CUAACACCAG   50

UCCCAGACGA CUCGCCCGA   69

( 2 ) INFORMATION FOR SEQ ID NO:142:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:142:

GGGAGGACGA UGCGGAUUCG AUUAGAGAUU GAACGAUCCU UUCAUCAGUU   50

GGAUCAGACG ACUCGCCCGA   70

( 2 ) INFORMATION FOR SEQ ID NO:143:

( i ) SEQUENCE CHARACTERISTICS:

(A) LENGTH: 71 base pairs
(B) TYPE: nucleic acid
(C) STRANDEDNESS: single
(D) TOPOLOGY: linear (ix) FEATURE:
(D) OTHER INFORMATION: All C's are 2'-F modified (ix) FEATURE:
(D) OTHER INFORMATION: All U's are 2'-F modified (xi) SEQUENCE DESCRIPTION: SEQ ID NO:143:

GGGAGGACGA UGCGGGGUUU UCUAAGUGUU GAACGAUCCU UCACAUAGCG 50

UGUCCCAGAC GACUCGCCCG A 71

(2) INFORMATION FOR SEQ ID NO:144:

(i) SEQUENCE CHARACTERISTICS:
(A) LENGTH: 70 base pairs
(B) TYPE: nucleic acid
(C) STRANDEDNESS: single
(D) TOPOLOGY: linear (ix) FEATURE:
(D) OTHER INFORMATION: All C's are 2'-F modified (ix) FEATURE:
(D) OTHER INFORMATION: All U's are 2'-F modified (xi) SEQUENCE DESCRIPTION: SEQ ID NO:144:

GGGAGGACGA UGCGGUAAGU UCUAACUUUU GAACGAUCCU UGGCACCCUG 50

ACUACAGACG ACUCGCCCGA 70

(2) INFORMATION FOR SEQ ID NO:145:

(i) SEQUENCE CHARACTERISTICS:
(A) LENGTH: 70 base pairs
(B) TYPE: nucleic acid
(C) STRANDEDNESS: single
(D) TOPOLOGY: linear (ix) FEATURE:
(D) OTHER INFORMATION: All C's are 2'-F modified (ix) FEATURE:
(D) OTHER INFORMATION: All U's are 2'-F modified (xi) SEQUENCE DESCRIPTION: SEQ ID NO:145:

GGGAGGACGA UGCGGACCGA CUAAAUGAUU GAACGAUCCU UAUUGUCUCU 50

AUCACAGACG ACUCGCCCGA 70

(2) INFORMATION FOR SEQ ID NO:146:

(i) SEQUENCE CHARACTERISTICS:
(A) LENGTH: 70 base pairs
(B) TYPE: nucleic acid
(C) STRANDEDNESS: single
(D) TOPOLOGY: linear (ix) FEATURE:
(D) OTHER INFORMATION: All C's are 2'-F modified (ix) FEATURE:
(D) OTHER INFORMATION: All U's are 2'-F modified (xi) SEQUENCE DESCRIPTION: SEQ ID NO:146:

GGGAGGACGA UGCGGUUUGA UGAGGUAGUU GAACGAUCCU UCCAUCCGUU 50

AGACCAGACG ACUCGCCCGA 70

( 2 ) INFORMATION FOR SEQ ID NO:147:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:147:

GGGAGGACGA UGCGGUUGGU UAUCCAUGUU GAACGUUCCU UCAUGUCGAA    50

UAUGCAGACG ACUCGCCCGA    70

( 2 ) INFORMATION FOR SEQ ID NO:148:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:148:

GGGAGGACGA UGCGGUUCAA CAACGUACUU GAACGAUCCU UGUGCUCGUU    50

GAUCCAGACG ACUCGCCCGA    70

( 2 ) INFORMATION FOR SEQ ID NO:149:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:149:

GGGAGGACGA UGCGGUUCGU UACGAUAAUU GAACGAUCCU UUUAUCUUUC    50

AGUCCAGACG ACUCGCCCGA    70

( 2 ) INFORMATION FOR SEQ ID NO:150:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:150:

```
GGGAGGACGA UGCGGUGCAU GAUUUAGUUG AACGAUCCUU CCAACUUCCA          50

GCACAGACGA CUCGCCCGA                                            69
```

(2) INFORMATION FOR SEQ ID NO:151:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ix) FEATURE:
        (D) OTHER INFORMATION: All C's are 2'-F modified (ix) FEATURE:
        (D) OTHER INFORMATION: All U's are 2'-F modified (xi) SEQUENCE DESCRIPTION: SEQ ID NO:151:

```
GGGAGGACGA UGCGGUUCAU UUUUGUGUUG AACGAUCCUU CACUAACCUA          50

CCACAGACGA CUCGCCCGA                                            69
```

(2) INFORMATION FOR SEQ ID NO:152:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ix) FEATURE:
        (D) OTHER INFORMATION: All C's are 2'-F modified (ix) FEATURE:
        (D) OTHER INFORMATION: All U's are 2'-F modified (xi) SEQUENCE DESCRIPTION: SEQ ID NO:152:

```
GGGAGGACGA UGCGGUUCUA GGUCGAAAUU GAACGAUCCU UUUUCGCUAU          50

GGAUCAGACG ACUCGCCCGA                                           70
```

(2) INFORMATION FOR SEQ ID NO:153:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ix) FEATURE:
        (D) OTHER INFORMATION: All C's are 2'-F modified (ix) FEATURE:
        (D) OTHER INFORMATION: All U's are 2'-F modified (xi) SEQUENCE DESCRIPTION: SEQ ID NO:153:

```
GGGAGGACGA UGCGGGUUUU CCUACUAGUU GAAUGAUCCU UCUAGUUAGA          50

UGCCAGACGA CUCGCCCGA                                            69
```

(2) INFORMATION FOR SEQ ID NO:154:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ix) FEATURE:
        (D) OTHER INFORMATION: All C's are 2'-F modified (ix) FEATURE:

( D ) OTHER INFORMATION: All U's are 2'-F modified ( x i ) SEQUENCE DESCRIPTION: SEQ ID NO:154:

GGGAGGACGA UGCGGGUUCC AGUAUUAGUU GAACGAUCCU UCUUAUCUGG    50

AGUCCAGACG ACUCGCCCGA    70

( 2 ) INFORMATION FOR SEQ ID NO:155:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:155:

GGGAGGACGA UGCGGUUUUA CUUAUUUAUU GAACGAUCCU UUUUCCCCUA    50

UGCCCAGACG ACUCGCCCGA    70

( 2 ) INFORMATION FOR SEQ ID NO:156:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:156:

GGGAGGACGA UGCGGACCGA CUAAAUGAUU GAACGAUCCU UAUUGUCUCU    50

AUCACAGACG ACUCGCCCGA    70

( 2 ) INFORMATION FOR SEQ ID NO:157:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-F modified ( i x ) FEATURE:
        ( D ) OTHER INFORMATION: All U's are 2'-F modified ( x i ) SEQUENCE DESCRIPTION: SEQ ID NO:157:

GGGAGGACGA UGCGGCAGUG UCAACAUCUU GAACGAUCCU UUUUUUCAGC    50

GCGUCAGACG ACUCGCCCGA    70

( 2 ) INFORMATION FOR SEQ ID NO:158:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear -continued ( i x ) FEATURE:
     ( D ) OTHER INFORMATION: All C's are 2'-F modified ( i x ) FEATURE:
     ( D ) OTHER INFORMATION: All U's are 2'-F modified ( x i ) SEQUENCE DESCRIPTION: SEQ ID NO:158:

GGGAGGACGA UGCGGUCAAU CAAGCUUCUU GAACGAUCCU UGAUUCGUAA       50

CUUCCAGACG ACUCGCCCGA       70

( 2 ) INFORMATION FOR SEQ ID NO:159:

( i ) SEQUENCE CHARACTERISTICS:
          ( A ) LENGTH: 70 base pairs
          ( B ) TYPE: nucleic acid
          ( C ) STRANDEDNESS: single
          ( D ) TOPOLOGY: linear ( i x ) FEATURE:
          ( D ) OTHER INFORMATION: All C's are 2'-F modified ( i x ) FEATURE:
          ( D ) OTHER INFORMATION: All U's are 2'-F modified ( x i ) SEQUENCE DESCRIPTION: SEQ ID NO:159:

GGGAGGACGA UGCGGUAACA GUCGAUUCUU GAACGAUCCU UUCCACUUCA       50

ACCGCAGACG ACUCGCCCGA       70

( 2 ) INFORMATION FOR SEQ ID NO:160:

( i ) SEQUENCE CHARACTERISTICS:
          ( A ) LENGTH: 70 base pairs
          ( B ) TYPE: nucleic acid
          ( C ) STRANDEDNESS: single
          ( D ) TOPOLOGY: linear ( i x ) FEATURE:
          ( D ) OTHER INFORMATION: All C's are 2'-F modified ( i x ) FEATURE:
          ( D ) OTHER INFORMATION: All U's are 2'-F modified ( x i ) SEQUENCE DESCRIPTION: SEQ ID NO:160:

GGGAGGACGA UGCGGUCUUA ACCUUUACUU GAACGACCCU UUAUUAGUUU       5

UUCUCAGACG ACUCGCCCGA       7